United States Patent
Matsuura et al.

(10) Patent No.: US 11,529,114 B2
(45) Date of Patent: Dec. 20, 2022

(54) INFORMATION PROCESSING APPARATUS, PROGRAM FOR OPERATING INFORMATION PROCESSING APPARATUS, METHOD FOR OPERATING INFORMATION PROCESSING APPARATUS, AND MAMMOGRAPHY APPARATUS

(71) Applicant: FUJIFILM Corporation, Tokyo (JP)

(72) Inventors: Masayoshi Matsuura, Kanagawa (JP); Ayako Muramoto, Kanagawa (JP); Takeyasu Kobayashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 391 days.

(21) Appl. No.: 16/561,038

(22) Filed: Sep. 5, 2019

(65) Prior Publication Data
US 2020/0100759 A1 Apr. 2, 2020

(30) Foreign Application Priority Data

Sep. 27, 2018 (JP) .............................. JP2018-182763

(51) Int. Cl.
*A61B 8/08* (2006.01)
*G06T 7/00* (2017.01)

(52) U.S. Cl.
CPC .......... *A61B 8/0825* (2013.01); *A61B 8/5207* (2013.01); *A61B 8/5269* (2013.01);
(Continued)

(58) Field of Classification Search
CPC ..... A61B 6/502; A61B 8/0825; A61B 8/5207; A61B 8/5269; A61B 8/085; A61B 8/0858;
(Continued)

(56) References Cited

U.S. PATENT DOCUMENTS 6,556,655 B1 * 4/2003 Chichereau ............ A61B 6/502
378/62
7,787,587 B2 * 8/2010 Tasaki .................... A61B 6/542
378/98.7
(Continued)

FOREIGN PATENT DOCUMENTS

JP 2007014525 1/2007
JP 2007117168 5/2007
(Continued)

OTHER PUBLICATIONS

"Search Report of Europe Counterpart Application", dated Feb. 27, 2020, p. 1-p. 8.
(Continued)

*Primary Examiner* — Carolyn A Pehlke
(74) *Attorney, Agent, or Firm* — JCIPRNET

(57) ABSTRACT

A control device of a mammography apparatus includes an acquisition unit that acquires a radiographic image as radiography information in a case in which the radiographic image of the breast is captured and a generation condition setting unit that sets generation conditions in a case in which an ultrasound image of the breast is generated, on the basis of the radiographic image acquired by the acquisition unit. The generation condition setting unit analyzes the radiographic image to detect the amount of mammary glands in the breast and sets, as the generation conditions, an amplification factor of an ultrasound image signal and a dynamic range which is a width of a grayscale value of the ultrasound image assigned to a value of the ultrasound image signal, according to the detected amount of mammary glands.

13 Claims, 21 Drawing Sheets

(52) U.S. Cl.
CPC .. *G06T 7/0012* (2013.01); *G06T 2207/10132* (2013.01); *G06T 2207/30068* (2013.01)

(58) Field of Classification Search
CPC .............. A61B 8/00; G06T 7/0012; G06T 2207/10132; G06T 2207/30068
See application file for complete search history.

(56) References Cited

U.S. PATENT DOCUMENTS

| | | | |
|---|---|---|---|
| 8,192,361 | B2 | 6/2012 | Sendai |
| 9,805,449 | B2 | 10/2017 | Morita |
| 2003/0158479 | A1* | 8/2003 | Li .................. G01S 7/52046 600/437 |
| 2008/0002872 | A1* | 1/2008 | Gatesoupe ............... G06T 7/11 382/132 |
| 2008/0234578 | A1* | 9/2008 | Claus ..................... G06T 7/38 600/437 |
| 2009/0086891 | A1* | 4/2009 | Ofuji ..................... A61B 6/463 378/37 |
| 2009/0118614 | A1 | 5/2009 | Sendai |
| 2009/0234229 | A1* | 9/2009 | Mikami .............. A61B 6/4494 600/445 |
| 2009/0252396 | A1* | 10/2009 | Morita .................. G06T 5/008 382/132 |
| 2010/0246924 | A1* | 9/2010 | Morita ................ A61B 5/4872 382/132 |
| 2011/0002519 | A1 | 1/2011 | Tomisaki et al. |
| 2011/0123074 | A1 | 5/2011 | Nie et al. |
| 2012/0029344 | A1 | 2/2012 | Nakayama |
| 2013/0123627 | A1 | 5/2013 | Oyama |
| 2014/0135623 | A1 | 5/2014 | Manak et al. |
| 2015/0093013 | A1 | 4/2015 | Morita |
| 2017/0128037 | A1 | 5/2017 | Mori et al. |
| 2017/0301095 | A1* | 10/2017 | Zhang ..................... G06T 5/007 |
| 2018/0365808 | A1* | 12/2018 | Jiang ....................... G06T 7/11 |

FOREIGN PATENT DOCUMENTS

| | | |
|---|---|---|
| JP | 2008161283 | 7/2008 |
| JP | 2009028381 | 2/2009 |
| JP | 2013102805 | 5/2013 |
| JP | 2014014655 | 1/2014 |
| JP | 2017051752 | 3/2017 |

OTHER PUBLICATIONS

"Office Action of Japan Counterpart Application", dated Aug. 10, 2021, with English translation thereof, p. 1-p. 9.

* cited by examiner

| AMPLIFICATION FACTOR DT | | 90 |
|---|---|---|
| AMOUNT OF MAMMARY GLANDS GV | AMPLIFICATION FACTOR GN | |
| 0 TO 25 | 1 | |
| 26 TO 50 | 1.25 | |
| 51 TO 75 | 1.5 | |
| 76 TO 100 | 2 | |
| ⋮ | ⋮ | |

SMALL ↓ LARGE

LOW ↓ HIGH

FIG. 11

| DYNAMIC RANGE DT | ~91 |
|---|---|
| AMOUNT OF MAMMARY GLANDS GV | DYNAMIC RANGE DR |
| 0 TO 25 | ULTRASOUND IMAGE SIGNAL — DR1 |
| 26 TO 50 | ULTRASOUND IMAGE SIGNAL — DR2 |
| 51 TO 75 | ULTRASOUND IMAGE SIGNAL — DR3 |
| 76 TO 100 | ULTRASOUND IMAGE SIGNAL — DR4 |
| ⋮ | ⋮ |

SMALL ↓ LARGE

NARROW ↓ WIDE

INFORMATION PROCESSING APPARATUS, PROGRAM FOR OPERATING INFORMATION PROCESSING APPARATUS, METHOD FOR OPERATING INFORMATION PROCESSING APPARATUS, AND MAMMOGRAPHY APPARATUS

CROSS-REFERENCE TO RELATED APPLICATION

This application claims priority from Japanese Patent Application No. 2018-182763, filed Sep. 27, 2018, the disclosure of which is incorporated herein by reference in its entirety.

BACKGROUND OF THE INVENTION

Technical Field

The technology according to the present disclosure relates to an information processing apparatus, a program for operating the information processing apparatus, a method for operating the information processing apparatus, and a mammography apparatus.

Related Art

A mammography apparatus has been known which captures a radiographic image of the breast. A technique has been proposed which captures an ultrasound image of the breast in addition to the radiographic image in order to increase the accuracy of detecting breast cancer in the mammography apparatus. For example, JP2008-161283A discloses a mammography apparatus comprising a radiation source that irradiates the breast with radiation, a radiation detector that detects the radiation transmitted through the breast, and an ultrasound transceiver including ultrasound transducers that transmit ultrasonic waves to the breast and receive ultrasound echoes from the breast.

In JP2008-161283A, a radiographic image is captured first and the captured radiographic image is analyzed to determine whether the breast included in the radiographic image is a dense breast (the amount of mammary glands is relatively large) or a fat breast (the amount of mammary glands is relatively small). Then, ultrasonic wave transmission conditions (a frequency, power (driving voltage), and a scanning speed) corresponding to the determination result are set. Specifically, in a case in which the breast is determined to be the dense breast, the scanning speed is reduced and power is increased.

One of the major factors that determine the quality of an ultrasound image is generation conditions in a case in which an ultrasound image is generated on the basis of ultrasound echoes. However, JP2008-161283A does not disclose the ultrasound image generation conditions.

An object of the technology according to the present disclosure is to provide an information processing apparatus that can set ultrasound image generation conditions contributing to improving the quality of an ultrasound image of the breast, a program for operating the information processing apparatus, a method for operating the information processing apparatus, and a mammography apparatus.

SUMMARY

In order to achieve the object, according to the present disclosure, there is provided an information processing apparatus comprising: an acquisition unit that acquires radiography information in a case in which a radiographic image of a breast is captured; and a generation condition setting unit that sets generation conditions in a case in which an ultrasound image of the breast is generated, on the basis of the radiography information acquired by the acquisition unit.

Preferably, the information processing apparatus further comprises a generation unit that generates the ultrasound image under the generation conditions set by the generation condition setting unit.

Preferably, the acquisition unit acquires the radiographic image as the radiography information, and the generation condition setting unit analyzes the radiographic image to detect an amount of mammary glands in the breast and sets the generation conditions corresponding to the detected amount of mammary glands.

Preferably, in a case in which an artifact is included in the breast, the generation condition setting unit removes an image of the artifact from the radiographic image and detects the amount of mammary glands.

Preferably, the acquisition unit acquires, as the radiography information, a compression thickness of the breast in a case in which the radiographic image is captured.

Preferably, the generation condition setting unit sets, as the generation conditions, at least one of an amplification factor of an ultrasound image signal which is an electric signal corresponding to ultrasound echoes reflected from the breast in a case in which ultrasonic waves are transmitted to the breast or a dynamic range which is a width of a grayscale value of the ultrasound image assigned to a value of the ultrasound image signal.

Preferably, the generation condition setting unit sets the amplification factor such that, as the amount of mammary glands becomes larger, the amplification factor becomes higher.

Preferably, the generation condition setting unit sets the dynamic range such that, as the amount of mammary glands becomes larger, the dynamic range becomes wider.

Preferably, the generation condition setting unit sets the amplification factor such that, as the compression thickness becomes larger, the amplification factor becomes higher.

Preferably, the generation condition setting unit sets the generation conditions for each of a plurality of regions.

Preferably, the information processing apparatus further comprises a transmission condition setting unit that sets transmission conditions of the ultrasonic waves transmitted to the breast on the basis of the radiography information acquired by the acquisition unit.

Preferably, the acquisition unit acquires, as the radiography information, a compression thickness of the breast in a case in which the radiographic image is captured, and the transmission condition setting unit sets a parameter for determining a depth of field of the ultrasonic waves as the transmission conditions.

Preferably, the transmission condition setting unit sets the parameter such that, as the compression thickness becomes larger, the depth of field becomes larger.

According to the present disclosure, there is provided a program for operating an information processing apparatus. The program causes a computer to function as: an acquisition unit that acquires radiography information in a case in which a radiographic image of a breast is captured; and a generation condition setting unit that sets generation conditions in a case in which an ultrasound image of the breast is generated, on the basis of the radiography information acquired by the acquisition unit.

According to the present disclosure, there is provided a method for operating an information processing apparatus. The method comprises: an acquisition step of acquiring radiography information in a case in which a radiographic image of a breast is captured; and a generation condition setting step of setting generation conditions in a case in which an ultrasound image of the breast is generated, on the basis of the radiography information acquired in the acquisition step.

According to the present disclosure, there is provided a mammography apparatus comprising: a radiation detector that detects radiation transmitted through a breast; an ultrasound transceiver including ultrasound transducers that transmit ultrasonic waves to the breast and receive ultrasound echoes from the breast; an acquisition unit that acquires radiography information in a case in which a radiographic image is captured by the radiation detector; and a generation condition setting unit that sets generation conditions in a case in which an ultrasound image is generated on the basis of the ultrasound echoes, on the basis of the radiography information acquired by the acquisition unit.

According to the technology of the present disclosure, it is possible to provide an information processing apparatus that can set ultrasound image generation conditions contributing to improving the quality of an ultrasound image of the breast, a program for operating the information processing apparatus, a method for operating the information processing apparatus, and a mammography apparatus.

BRIEF DESCRIPTION OF THE DRAWINGS

Exemplary embodiments according to the technique of the present disclosure will be described in detail based on the following figures, wherein:

FIG. 11 is a diagram illustrating a dynamic range data table;

DETAILED DESCRIPTION

First Embodiment

Figure 1:
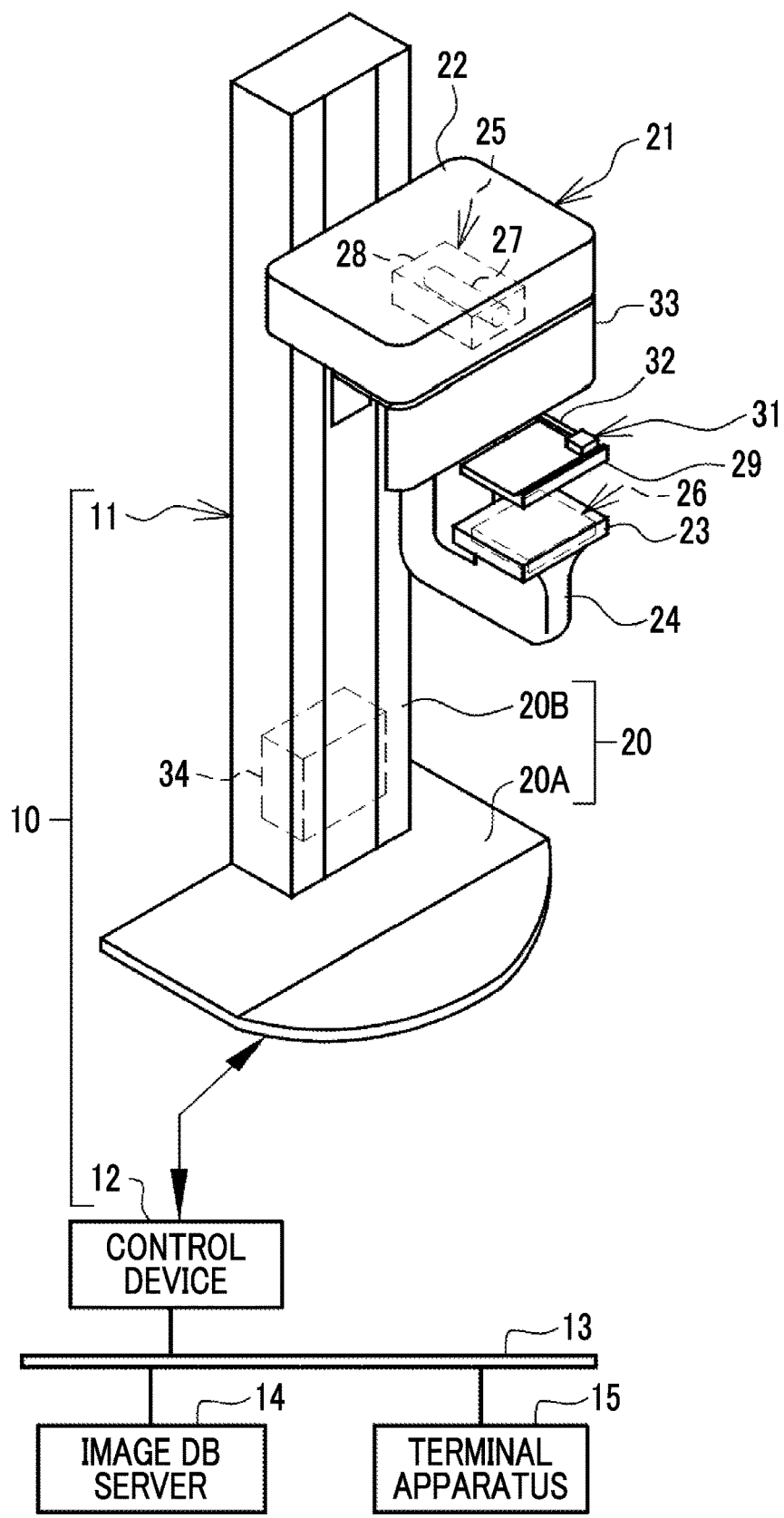
FIG. 1 is a diagram illustrating, for example, a mammography apparatus.
Figure 2:
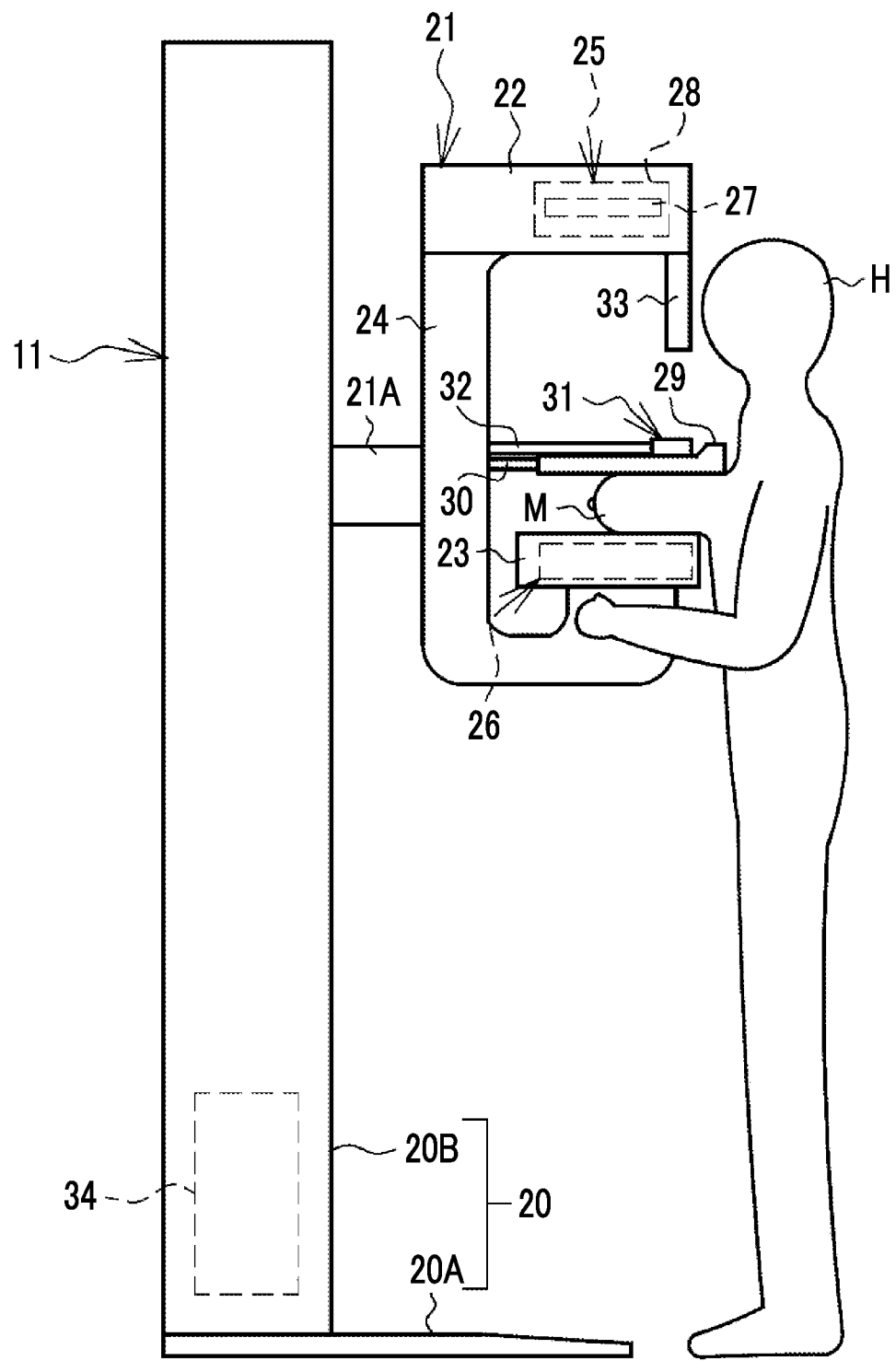
FIG. 2 is a diagram illustrating an apparatus main body of the mammography apparatus.

In FIGS. 1 and 2, a mammography apparatus 10 uses a breast M of a subject H as an object. The mammography apparatus 10 irradiates the breast M with radiation R (see FIG. 3), such as X-rays or γ-rays, to capture a radiographic image of the breast M. In addition, the mammography apparatus 10 transmits ultrasonic waves US (see FIG. 5) to the breast M, receives ultrasound echoes UE (see FIG. 5) reflected from the breast M, and captures an ultrasound image (for example, a B-mode image) of the breast M. The capture of a radiographic image is performed before the capture of an ultrasound image. In the following description, in some cases, the capture of a radiographic image is referred to as radiography and the capture of an ultrasound image is referred to as ultrasound imaging.

The mammography apparatus 10 includes an apparatus main body 11 and a control device 12 corresponding to an information processing apparatus. The apparatus main body 11 is installed, for example, in a radiography room of a medical facility. The control device 12 is a computer, such as a personal computer or a workstation, and is installed, for example, in a control room next to the radiography room. The control device 12 is connected to an image database (hereinafter, referred to as DB) server 14 through a network 13, such as a local area network (LAN), such that it can communicate with the image DB server. The image DB server 14 receives a radiographic image and an ultrasound image from the mammography apparatus 10, and accumulates and manages the radiographic image and the ultrasound image.

A terminal apparatus 15 is also connected to the network 13. The terminal apparatus 15 is, for example, a personal computer that is used by a doctor to make a diagnosis based on the radiographic image and the ultrasound image. The terminal apparatus 15 receives the radiographic image and the ultrasound image from the image DB server 14 and displays the radiographic image and the ultrasound image on a display.

The apparatus main body 11 includes a stand 20 and an arm 21. The stand 20 includes a pedestal 20A that is provided on the floor of the radiography room and a support 20B that extends from the pedestal 20A in a height direction. The arm 21 has a substantially C-shape in a side view and is connected to the support 20B through a connection portion 21A. The arm 21 can be moved with respect to the support 20B in the height direction by the connection portion 21A and the height of the arm 21 can be adjusted according to the height of the subject H by the connection portion 21A. In addition, the arm 21 is rotatable on a rotation axis perpendicular to the support 20B through the connection portion 21A.

The arm 21 includes a radiation generation portion 22, an imaging table 23, and a main body portion 24. The radiation generation portion 22 accommodates a radiation source 25. The breast M is placed on the imaging table 23. In addition, the imaging table 23 accommodates a radiation detector 26. The main body portion 24 integrally connects the radiation generation portion 22 and the imaging table 23. The radiation generation portion 22 is provided on the upper side in the height direction and the imaging table 23 is provided on the lower side in the height direction at a posture where the imaging table 23 faces the radiation generation portion 22.

The radiation source 25 includes a radiation tube 27 and a housing 28 that accommodates the radiation tube 27. The radiation detector 26 detects the radiation R transmitted through the breast M and outputs a radiographic image.

A compression plate 29 is attached between the radiation generation portion 22 and the imaging table 23 in the main body portion 24. The compression plate 29 is made of a material that transmits the radiation R, the ultrasonic waves US, and the ultrasound echoes UE. The compression plate 29 is made of a resin, such as polymethylpentene, polycarbonate, acryl, or polyethylene terephthalate. In particular, polymethylpentene has low rigidity, high elasticity, and high flexibility. In addition, for polymethylpentene, acoustic impedance that affects the reflectivity of the ultrasonic waves US and the ultrasound echoes UE and an attenuation coefficient that affects the attenuation of the ultrasonic waves US and the ultrasound echoes UE are appropriate values. Therefore, polymethylpentene is suitable as the material forming the compression plate 29.

The compression plate 29 is provided so as to face the imaging table 23. The compression plate 29 can be moved in a direction toward the imaging table 23 and a direction away from the imaging table 23 by a movement mechanism 30. The compression plate 29 is moved to the imaging table 23 and compresses the breast M interposed between the compression plate 29 and the imaging table 23.

An ultrasound transceiver 31 is provided on a surface of the compression plate 29 which is close to the radiation generation portion 22. The ultrasound transceiver 31 can be moved in the direction toward the imaging table 23 and the direction away from the imaging table 23 by a scanning mechanism 32 in operative association with the movement of the compression plate 29. In addition, the ultrasound transceiver 31 is moved by the scanning mechanism 32 in an S-shape on the surface of the compression plate 29 which is close to the radiation generation portion 22 in a depth direction (a direction toward the subject H and a direction away from the subject H) and a lateral direction perpendicular to the height direction and the depth direction.

A face guard 33 is attached to a lower part of the front surface of the radiation generation portion 22. The face guard 33 protects the face of the subject H from the radiation R.

A voltage generator 34 that generates a tube voltage applied to the radiation tube 27 is provided in the support 20B. In addition, a voltage cable (not illustrated) that extends from the voltage generator 34 is provided in the support 20B. The voltage cable further extends from the connection portion 21A into the radiation generation portion 22 through the arm 21 and is connected to the radiation source 25.

Figure 3:
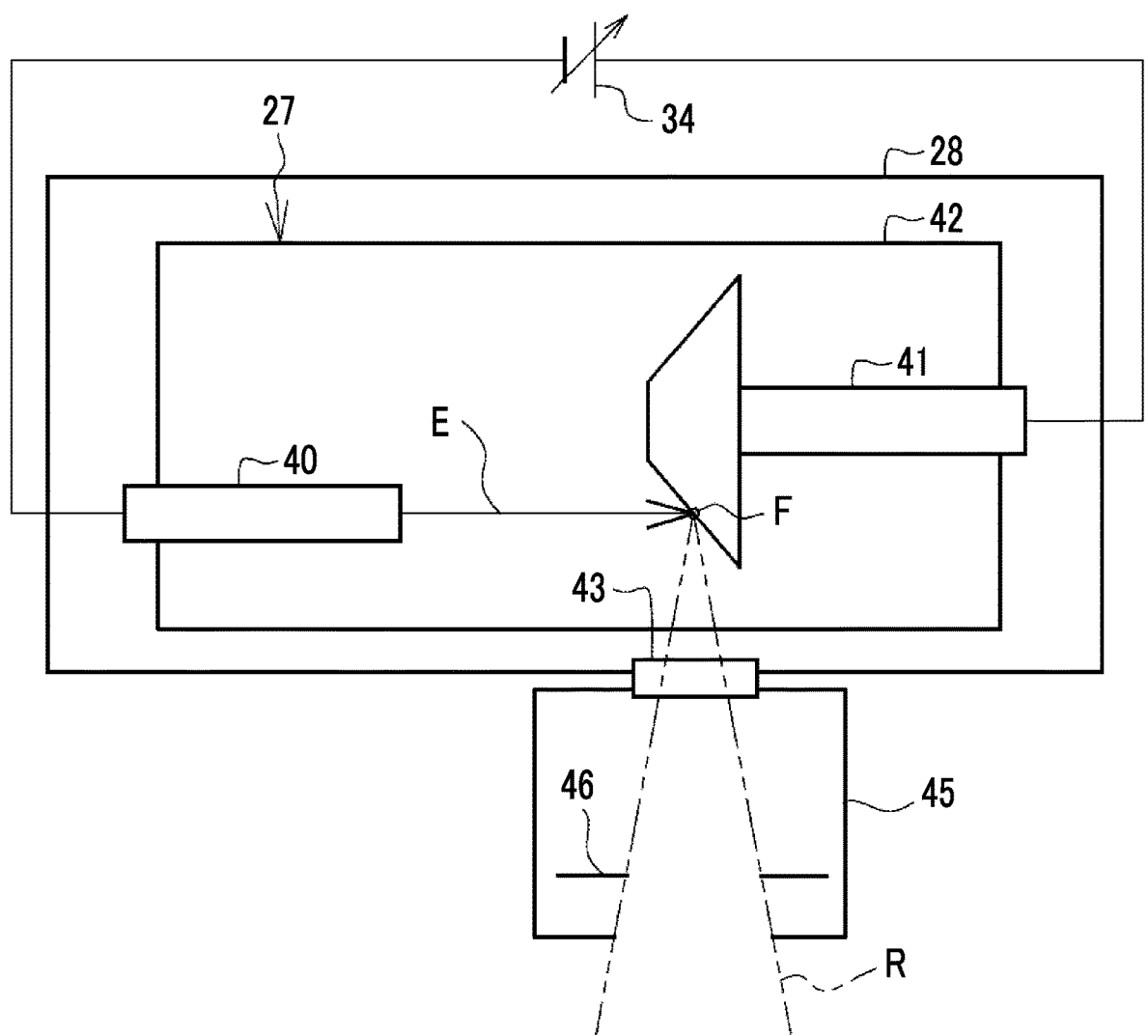
FIG. 3 is a diagram illustrating a radiation tube.

In FIG. 3, the radiation tube 27 includes a cathode 40 and an anode 41. The cathode 40 emits electrons E. The electrons E collide with the anode 41 and the anode 41 emits the radiation R. The cathode 40 and the anode 41 are accommodated in a vacuum glass tube 42. The anode 41 is a rotating anode that is rotated by a rotation mechanism.

The voltage generator 34 applies a tube voltage between the cathode 40 and the anode 41. The electrons E are emitted from the cathode 40 to the anode 41 by the application of the tube voltage. Then, the radiation R is emitted from a point (focus) F of the anode 41 where the electrons E collide.

The housing 28 is provided with a radiation transmission window 43 that transmits the radiation R. The radiation R emitted from the anode 41 is emitted to the outside of the housing 28 through the radiation transmission window 43. In addition, the housing 28 is filled with insulating oil.

An irradiation field limiter 45 (not illustrated in FIGS. 1 and 2) is provided below the radiation transmission window 43 in the height direction. The irradiation field limiter 45 is also called a collimator and sets the irradiation field of the radiation R in a radiography region 55 (see FIG. 6) of the radiation detector 26. Specifically, the irradiation field limiter 45 includes a plurality of shielding plates 46 which are made of, for example, lead and shield the radiation R transmitted through the radiation transmission window 43. The shielding plates 46 are moved to change the size of, for example, a rectangular irradiation opening defined by the shielding plates 46 to set the irradiation field of the radiation R.

Figure 4:
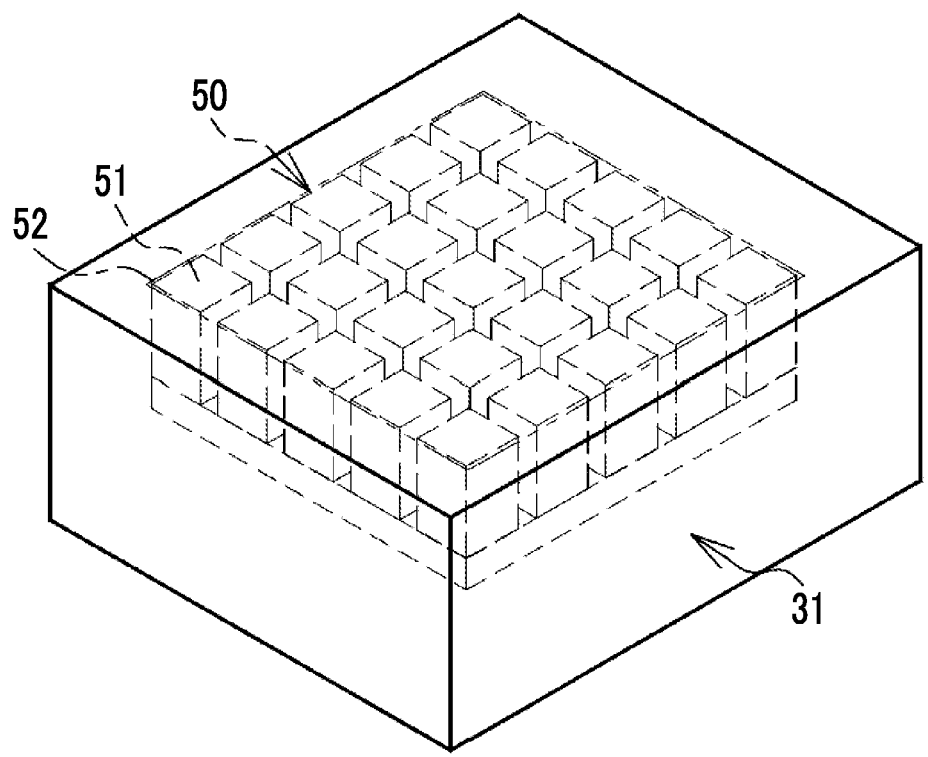
FIG. 4 is a diagram illustrating the internal structure of an ultrasound transceiver.

In FIG. 4 illustrating the ultrasound transceiver 31 as viewed from the radiation detector 26, the ultrasound transceiver 31 has an ultrasound transducer array 50. The ultrasound transducer array 50 is configured by two-dimensionally arranging a plurality of ultrasound transducers 51. As is well known, the ultrasound transducer 51 is configured by forming electrodes at both ends of a piezoelectric body, such as a piezoelectric ceramic typified by lead (Pb) zirconatetitanate (PZT) or a polymeric piezoelectric element typified by polyvinylidene difluoride (PVDF). An arrangement surface of the ultrasound transducers 51 defines an ultrasound imaging region 52 which captures an ultrasound image of the breast M.

Figure 5:
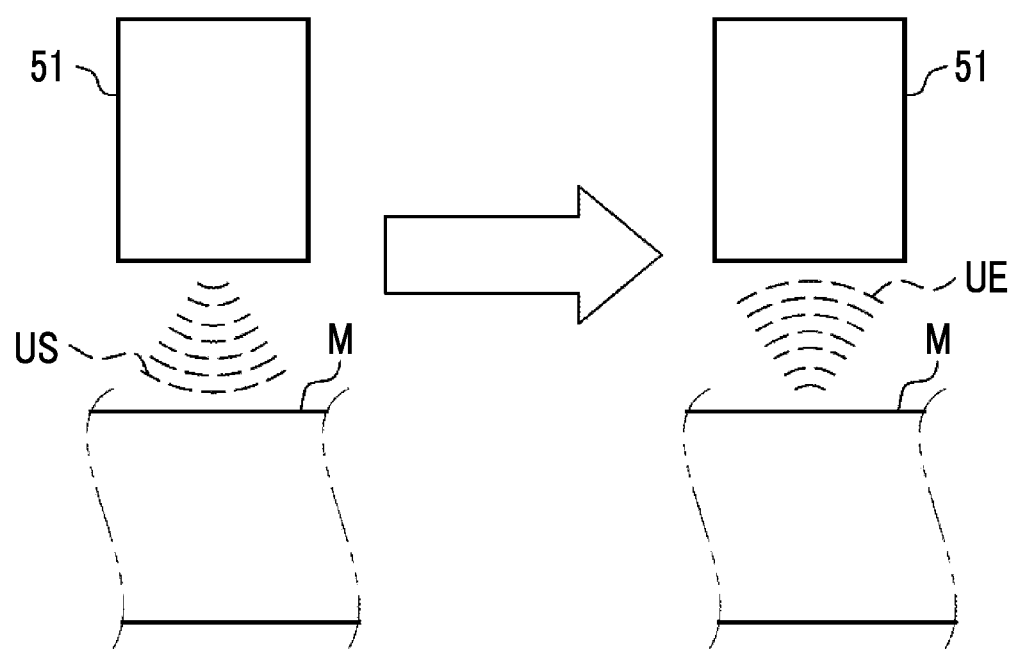
FIG. 5 is a diagram illustrating an aspect in which the ultrasound transducer transmits ultrasonic waves to the breast and receives ultrasound echoes from the breast.

As illustrated on the left side of an arrow in FIG. 5, the ultrasound transducer 51 transmits the ultrasonic waves US to the breast M. In addition, as illustrated on the right side of the arrow, the ultrasound transducer 51 receives the ultrasound echoes UE which are reflected waves of the ultrasonic waves US from the breast M. In FIG. 5, for example, the compression plate 29 is not illustrated for simplicity of illustration.

Figure 6:
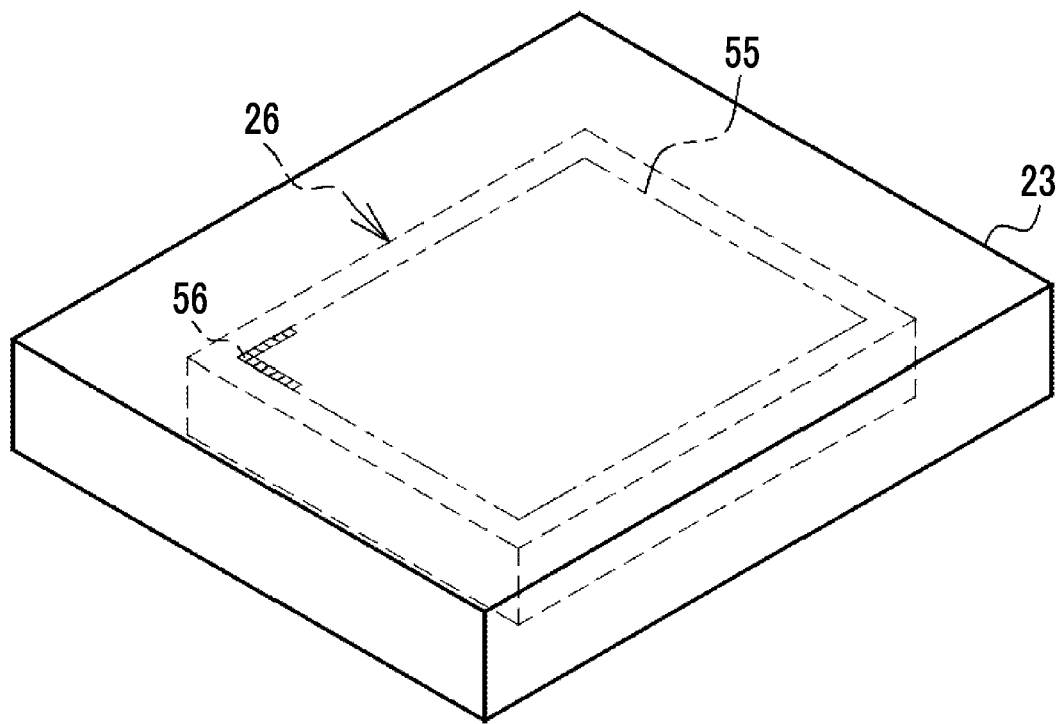
FIG. 6 is a diagram illustrating an imaging table.

In FIG. 6, the radiation detector 26 has the radiography region 55. The radiography region 55 is a region which detects the radiation R transmitted through the breast M and captures a radiographic image of the breast M. Specifically, the radiography region 55 is a region in which pixels 56 converting the radiation R into an electric signal (hereinafter, referred to as a radiographic image signal) are two-dimensionally arranged. The radiation detector 26 is referred to as a flat panel detector (FPD). The radiation detector 26 may be an indirect conversion type that includes, for example, a scintillator converting the radiation R into visible light and converts visible light emitted from the scintillator into a radiographic image signal or a direct conversion type that directly converts the radiation R into a radiographic image signal.

For example, the mammography apparatus 10 captures the image of the breast M using two imaging methods, that is, a craniocaudal view (CC) imaging method and a mediolateral oblique view (MLO) imaging method. The CC imaging is an imaging method which captures an image while compressing the breast M interposed between the imaging table 23 and the compression plate 29 in the vertical direction. In contrast, the MLO imaging is an imaging method which captures an image while compressing the breast M interposed between the imaging table 23 and the compression plate 29 at an inclination angle of about 60°.

Figure 7:
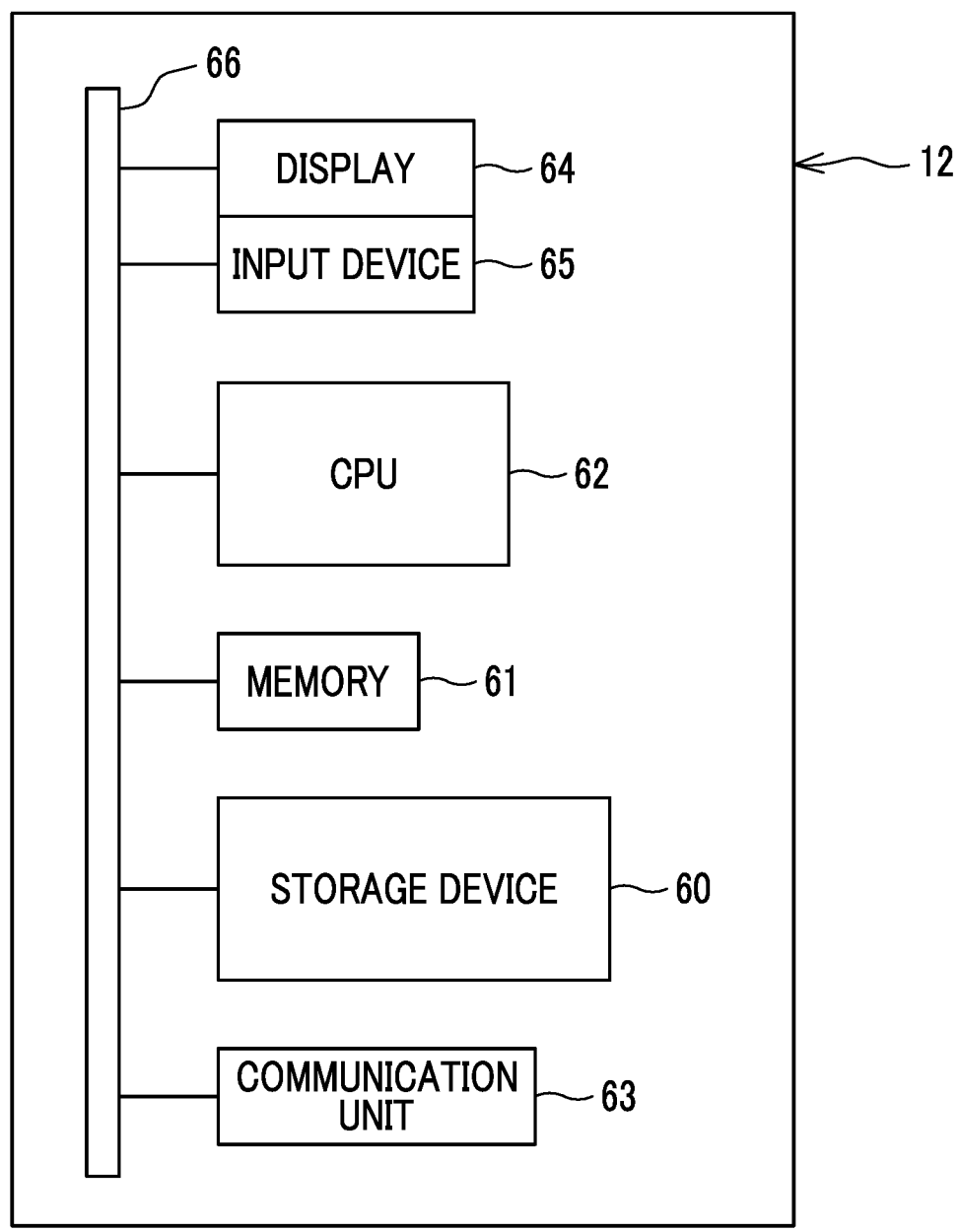
FIG. 7 is a block diagram illustrating a computer forming a control device.

In FIG. 7, a computer forming the control device 12 comprises a storage device 60, a memory 61, a central processing unit (CPU) 62 corresponding to a control unit, a communication unit 63, a display 64, and an input device 65. These components are connected to each other through a data bus 66.

The storage device 60 is a hard disk drive that is provided in the computer forming the control device 12 or is connected to the computer through a cable or a network. Alternatively, the storage device 60 is a disk array formed by connecting a plurality of hard disk drives. The storage device 60 stores a control program, such as an operating system, various application programs, and various types of data associated with these programs.

The memory 61 is a work memory that is used by the CPU 62 to perform processes. The CPU 62 loads the program stored in the storage device 60 to the memory 61 and performs the process based on the program to control the overall operation of each unit of the computer.

The communication unit 63 is a network interface that controls the transmission of various kinds of information through the network 13. The display 64 displays various screens. The various screens have an operation function by a graphic user interface (GUI). The computer forming the control device 12 receives the input of an operation command from the input device 65 through various screens. The input device 65 is, for example, a keyboard, a mouse, and a touch panel.

Figure 8:
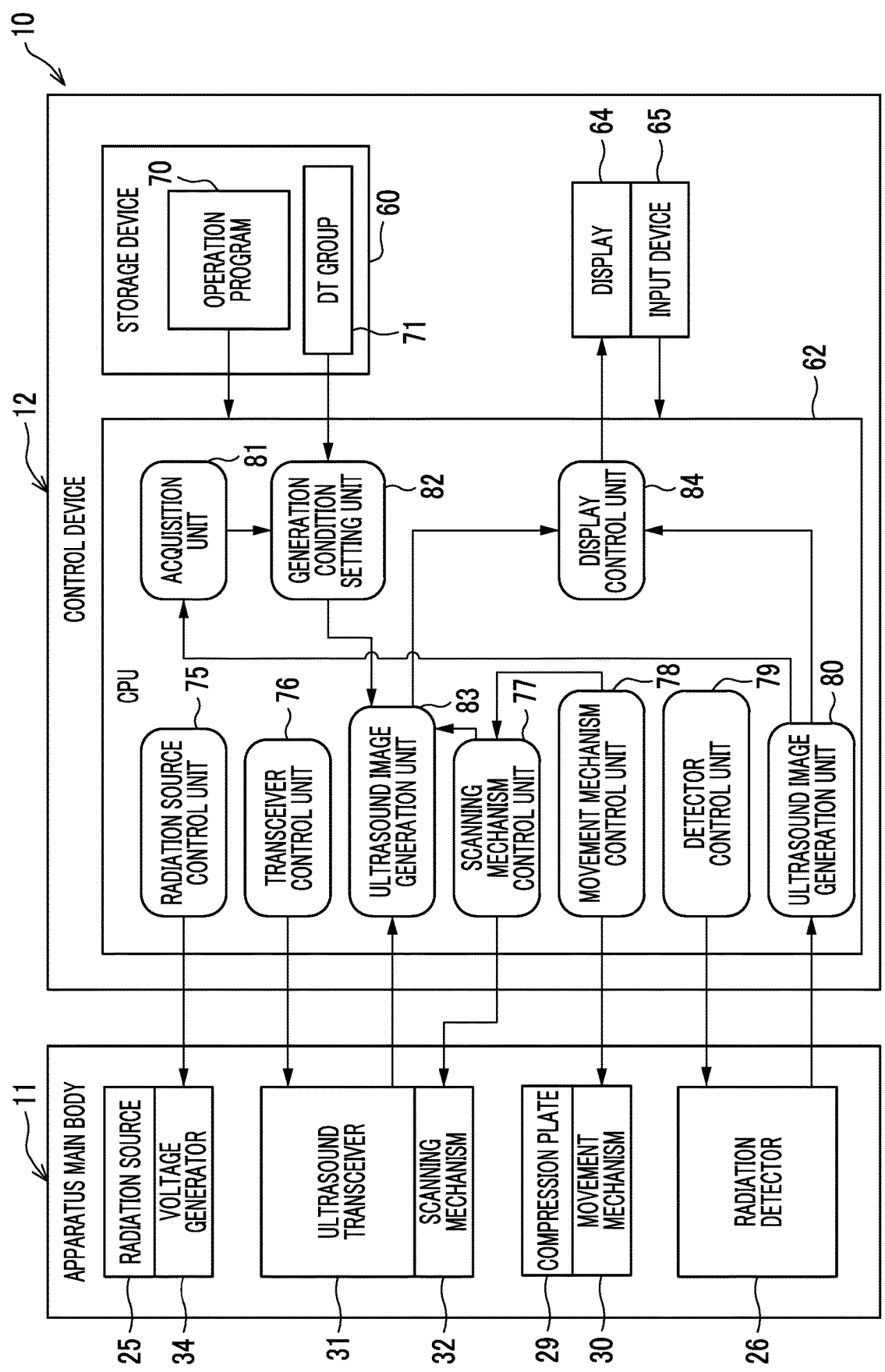
FIG. 8 is a block diagram illustrating each processing unit of a CPU of the control device.

In FIG. 8, an operation program 70 is stored as an application program in the storage device 60 of the control device 12. The operation program 70 is an application program that causes the computer forming the control device 12 to function as an information processing apparatus. The storage device 60 stores a data table (hereinafter, referred to as DT) group 71 in addition to the operation program 70.

In a case in which the operation program 70 starts, the CPU 62 of the computer forming the control device 12 functions as a radiation source control unit 75, a transceiver control unit 76, a scanning mechanism control unit 77, a movement mechanism control unit 78, a detector control unit 79, a radiographic image generation unit 80, an acquisition unit 81, a generation condition setting unit 82, an ultrasound image generation unit 83 corresponding to a generation unit, and a display control unit 84 in cooperation with, for example, the memory 61.

The radiation source control unit 75 controls the operation of the voltage generator 34 to control the operation of the radiation source 25. Specifically, the radiation source control unit 75 sets the irradiation conditions of the radiation R input through the input device 65 to the voltage generator 34. The irradiation conditions include the tube voltage applied from the voltage generator 34 to the radiation tube 27, a tube current, and the irradiation time of the radiation R. Each value of the irradiation conditions is adjusted such that the density of the radiographic image is at a substantially constant level regardless of an individual difference in the breast M. Instead of the tube current and the irradiation time, a tube current-irradiation time product (so-called mAs value) may be used as the irradiation conditions.

In addition, the radiation source control unit 75 controls the irradiation field limiter 45 such that the shielding plate 46 of the irradiation field limiter 45 is moved to set the irradiation field.

The transceiver control unit 76 controls the operation of the ultrasound transceiver 31. The transceiver control unit 76 controls the transmission timing of the ultrasonic waves US from each ultrasound transducer 51 such that a plurality of ultrasound transducers 51 of the ultrasound transceiver 31 sequentially transmit the ultrasonic waves US to the breast M. In addition, the transceiver control unit 76 directs each ultrasound transducer 51 to receive the ultrasound echoes UE and to output an electric signal (hereinafter, referred to as an ultrasound image signal) corresponding to the received ultrasound echoes UE to the ultrasound image generation unit 83.

The scanning mechanism control unit 77 controls the operation of the scanning mechanism 32. The scanning mechanism control unit 77 operates the scanning mechanism 32 in operative association with the movement of the compression plate 29 by the movement mechanism 30 to move the ultrasound transceiver 31 in the direction toward the imaging table 23 and the direction away from the imaging table 23. In addition, the scanning mechanism control unit 77 operates the scanning mechanism 32 such that the ultrasound transceiver 31 is moved for scanning on the surface of the compression plate 29 which is close to the radiation generation portion 22 in the depth direction and the lateral direction. In the scanning process, the transceiver control unit 76 directs the ultrasound transducer 51 to transmit the ultrasonic waves US, to receive the ultrasound echoes UE, and to output an ultrasound image signal.

The scanning mechanism control unit 77 controls the scanning mechanism 32 such that the ultrasound transceiver 31 scans almost the same region as the radiography region 55 of the radiation detector 26. Therefore, the ultrasound transceiver 31 scans the entire region which has almost the same size as the radiography region 55 and has almost the same positional relationship with the breast M as the radiography region 55.

The movement mechanism control unit 78 controls the operation of the movement mechanism 30. Specifically, the movement mechanism control unit 78 operates the movement mechanism 30 to move the compression plate 29 in the direction toward the imaging table 23 and the direction away from the imaging table 23.

The movement mechanism 30 is provided with a pressure sensor (not illustrated) that measures the compression pressure of the compression plate 29 against the breast M. The compression pressure measured by the pressure sensor is input to the movement mechanism control unit 78. The movement mechanism control unit 78 moves the compression plate 29 such that the compression pressure falls within a prescribed range.

The detector control unit 79 controls the operation of the radiation detector 26. The detector control unit 79 directs the pixels 56 of the radiation detector 26 to start to accumulate charge which is the source of a radiographic image signal in synchronization with the irradiation start timing of the radiation R from the radiation source 25. In addition, the detector control unit 79 reads the accumulated charge from the pixels 56 in synchronization with the irradiation end timing of the radiation R from the radiation source 25 and outputs the charge as a radiographic image signal to the radiographic image generation unit 80.

The radiographic image generation unit 80 generates a radiographic image on the basis of the radiographic image signal from the radiation detector 26. The radiographic image generation unit 80 outputs the generated radiographic image to the acquisition unit 81 and the display control unit 84.

The acquisition unit 81 acquires the radiographic image from the radiographic image generation unit 80 as radiography information in a case in which the radiographic image of the breast M is captured. The acquisition unit 81 outputs the acquired radiographic image to the generation condition setting unit 82. The radiography information is information obtained by radiography in which the imaging table 23 and the compression plate 29 start to compress the breast M, the radiation source 25 emits the radiation R in this state, the radiation detector 26 outputs a radiographic image signal, and the radiographic image generation unit 80 generates a radiographic image.

The generation condition setting unit 82 sets generation conditions in a case in which an ultrasound image of the breast M is generated, on the basis of the radiographic image from the acquisition unit 81 and the DT group 71. The generation condition setting unit 82 outputs the set generation conditions to the ultrasound image generation unit 83.

The ultrasound image generation unit 83 generates an ultrasound image under the generation conditions from the generation condition setting unit 82 on the basis of the ultrasound image signal from the ultrasound transceiver 31. The ultrasound image generation unit 83 outputs the generated ultrasound image to the display control unit 84.

The display control unit 84 performs control such that various screens are displayed on the display 64. Specifically, the display control unit 84 performs control such that, for example, an irradiation condition input screen (not illustrated) for receiving the input of the irradiation conditions of the radiation R and an image display screen 100 (see FIG. 16) for displaying the radiographic image from the radiographic image generation unit 80 and the ultrasound image from the ultrasound image generation unit 83 side by side are displayed on the display 64.

Figures 9, 10:
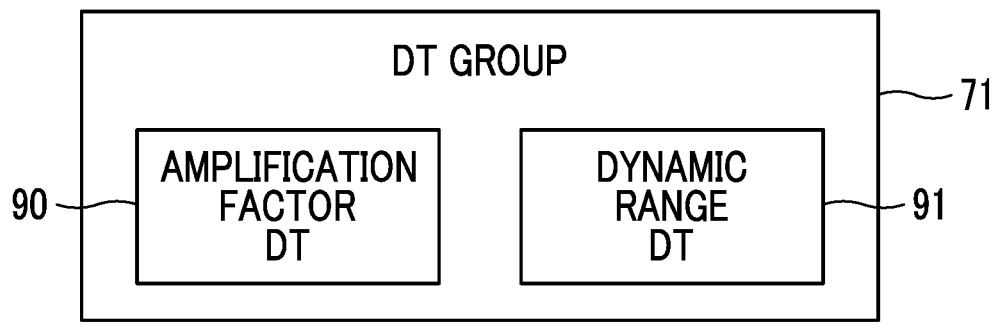
FIG. 9 is a diagram illustrating a data table group.
FIG. 10 is a diagram illustrating an amplification factor data table.

As illustrated in FIG. 9, the DT group 71 has an amplification factor DT90 and a dynamic range DT91. Here, the amplification factor is a value that is multiplied by the ultrasound image signal from the ultrasound transceiver 31 to amplify the ultrasound image signal in the ultrasound image generation unit 83 and is also called gain. In addition, the dynamic range is the width of a grayscale value of the ultrasound image which is assigned to the value of the ultrasound image signal from the ultrasound transceiver 31 in the ultrasound image generation unit 83.

As illustrated in FIG. 10, an amplification factor GN corresponding to each range of the amount of mammary glands GV of the breast M is registered in the amplification factor DT 90. The amount of mammary glands GV is literally the amount of mammary glands in the breast M.

The amplification factor GN is 1 in a case in which the amount of mammary glands GV is in the range of 0 to 25. That is, no amplification is performed in the range. For example, the amplification factor GN is 1.25 in a case in which the amount of mammary glands GV is in the range of 26 to 50, is 1.5 in a case in which the amount of mammary glands GV is in the range of 51 to 75, and is 2 in a case in which the amount of mammary glands GV is in the range of 76 to 100. That is, the amplification factor DT 90 is set such that, as the amount of mammary glands GV becomes larger, the amplification factor GN becomes higher.

As illustrated in FIG. 11, a dynamic range DR corresponding to each range of the amount of mammary glands GV is registered in the dynamic range DT 91. A dynamic range DR1 which is set to a relatively narrow range from a minimum value MIN of the ultrasound image signal is registered so as to correspond to a case in which the amount of mammary glands GV is in the range of 0 to 25. A dynamic range DR2 which is set to a range that is slightly extended to a maximum value MAX of the ultrasound image signal from the range in the case in which the amount of mammary glands GV is in the range of 0 to 25 is registered so as to correspond to a case in which the amount of mammary glands GV is in the range of 26 to 50. Similarly, the dynamic range DR which is set to a range that is more extended to the maximum value MAX as the amount of mammary glands GV becomes larger is registered. That is, the dynamic range DT 91 is set such that, as the amount of mammary glands GV becomes larger, the dynamic range DR becomes wider.

The setting of the value of the amplification factor GN illustrated in FIG. 10 and the setting of the position and width of the dynamic ranges DR1 to DR4 illustrated in FIG. 11 are just an example. In addition, the amplification factor GN may not be necessarily in the form of a data table such as the amplification factor DT 90. For example, an expression in which the amount of mammary glands GV is a parameter and the amplification factor GN is a solution may be used. Similarly, the position and width of the dynamic range DR may be calculated by an expression having the amount of mammary glands GV as parameter.

Figure 12:
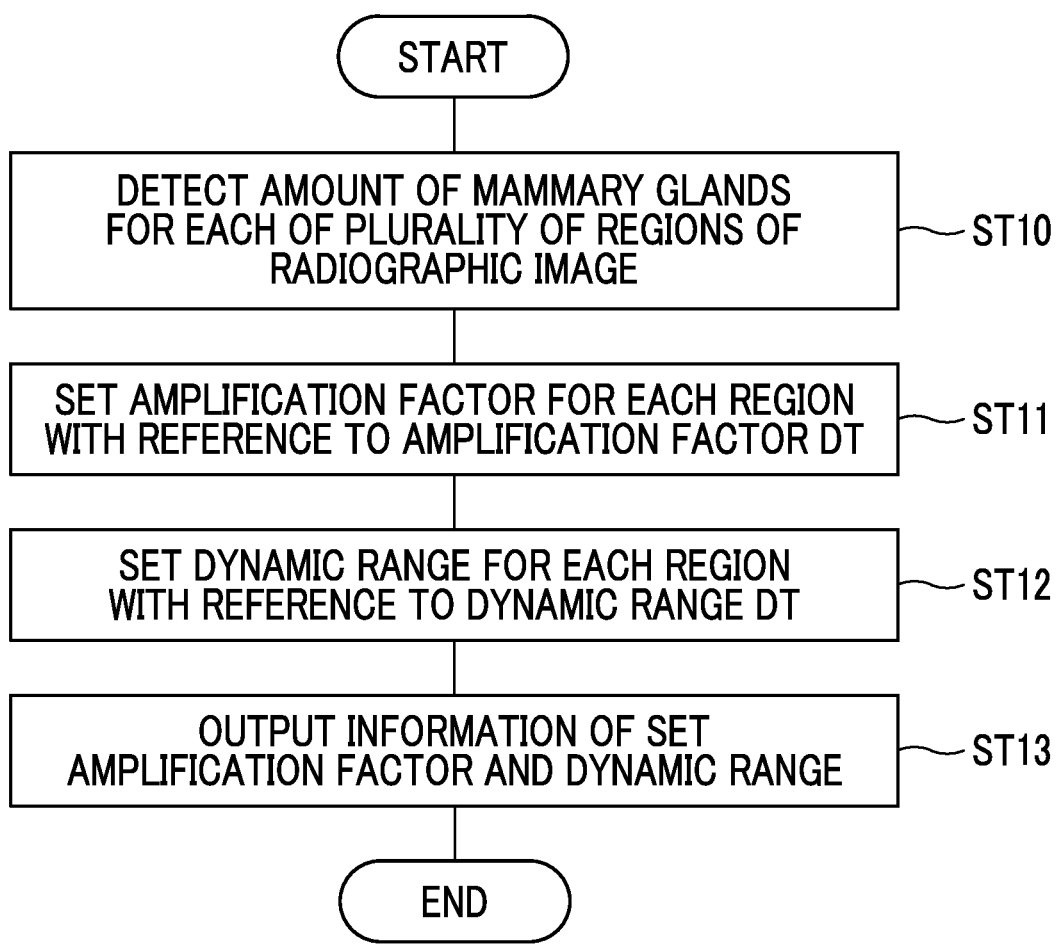
FIG. 12 is a flowchart illustrating the flow of a process of a generation condition setting unit.

FIG. 12 is a flowchart illustrating the procedure of setting the generation conditions in the generation condition setting unit 82. First, the generation condition setting unit 82 detects the amount of mammary glands GV for each of a plurality of regions of the radiographic image (Step ST10). A known method, such as a technique disclosed in JP2010-253245A which estimates a mammary gland content on the basis of a radiographic image and a fat image estimated from the radiographic image, is used as a method for detecting the amount of mammary glands GV from the radiographic image.

Then, the generation condition setting unit 82 sets the amplification factor GN corresponding to the detected amount of mammary glands GV for each region with reference to the amplification factor DT 90 (Step ST11). In addition, the generation condition setting unit 82 sets the dynamic range DR corresponding to the detected amount of mammary glands GV for each region with reference to the dynamic range DT 91 (Step ST12). Then, the generation condition setting unit 82 outputs the information of the set amplification factor GN and dynamic range DR to the ultrasound image generation unit 83 (Step ST13).

Figure 13:
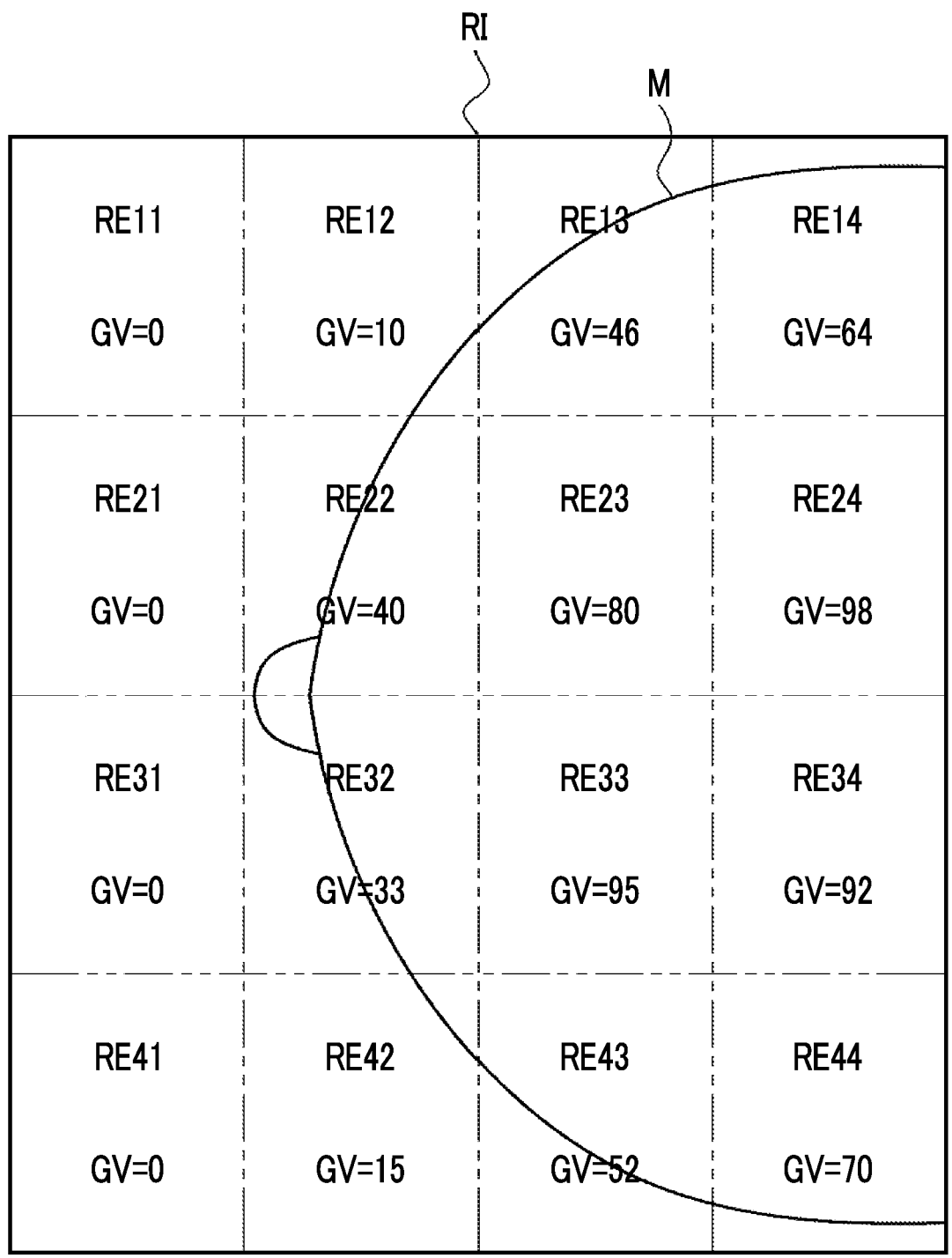
FIG. 13 is a diagram illustrating an aspect in which the amount of mammary glands is detected for each of a plurality of regions of a radiographic image.

FIG. 13 illustrates an aspect in which the amount of mammary glands GV is detected for each of a total of 16 regions RE11, RE12, ..., RE43, and RE44 of a radiographic image RI in Step ST10. Since the breast M is not included in the regions RE11, RE21, RE31, and RE41, the amount of mammary glands GV in the regions is 0. The breast M is included in the other regions RE and the amount of mammary glands GV corresponding to a portion in which the breast M is included is detected. For example, the amount of mammary glands GV in the region RE23 is 80. The amount of mammary glands GV in the region RE14 is 64. The number of regions RE may be less than or greater than 16 described as an example. One pixel 56 may be used as one region RE. In addition, the outline of the breast M may be extracted by a known image recognition technique and the amount of mammary glands GV may not be detected for the region RE without including the breast M.

Figure 14:
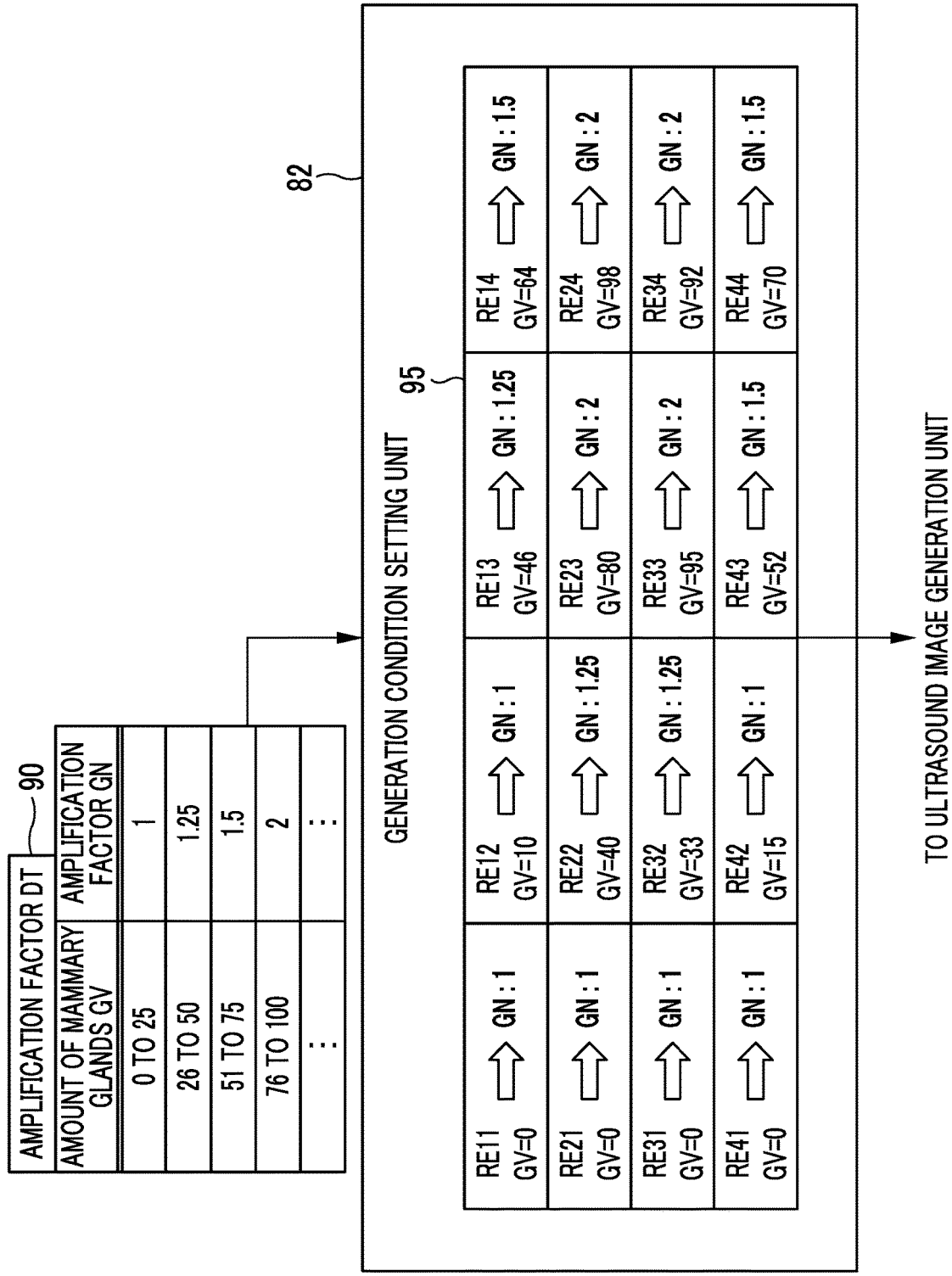
FIG. 14 is a diagram illustrating an aspect in which an amplification factor is set for each region as generation conditions.

In FIG. 14 illustrated in Step ST11, the generation condition setting unit 82 sets the amplification factor GN for each region RE as illustrated in a table 95. For example, in the regions RE11, RE12, RE21, RE31, RE41, and RE42, since the amount of mammary glands GV is in the range of 0 to 25, the amplification factor GN is set to 1. In the regions RE23, RE24, RE33, and RE34, since the amount of mammary glands GV is in the range of 76 to 100, the amplification factor GN is set to 2. That is, the generation condition setting unit 82 sets the amplification factor GN for each of the plurality of regions RE such that, as the amount of mammary glands GV becomes larger, the amplification factor GN becomes higher. The generation condition setting unit 82 outputs the information of the amplification factor GN set for each region RE to the ultrasound image generation unit 83.

Figure 15:
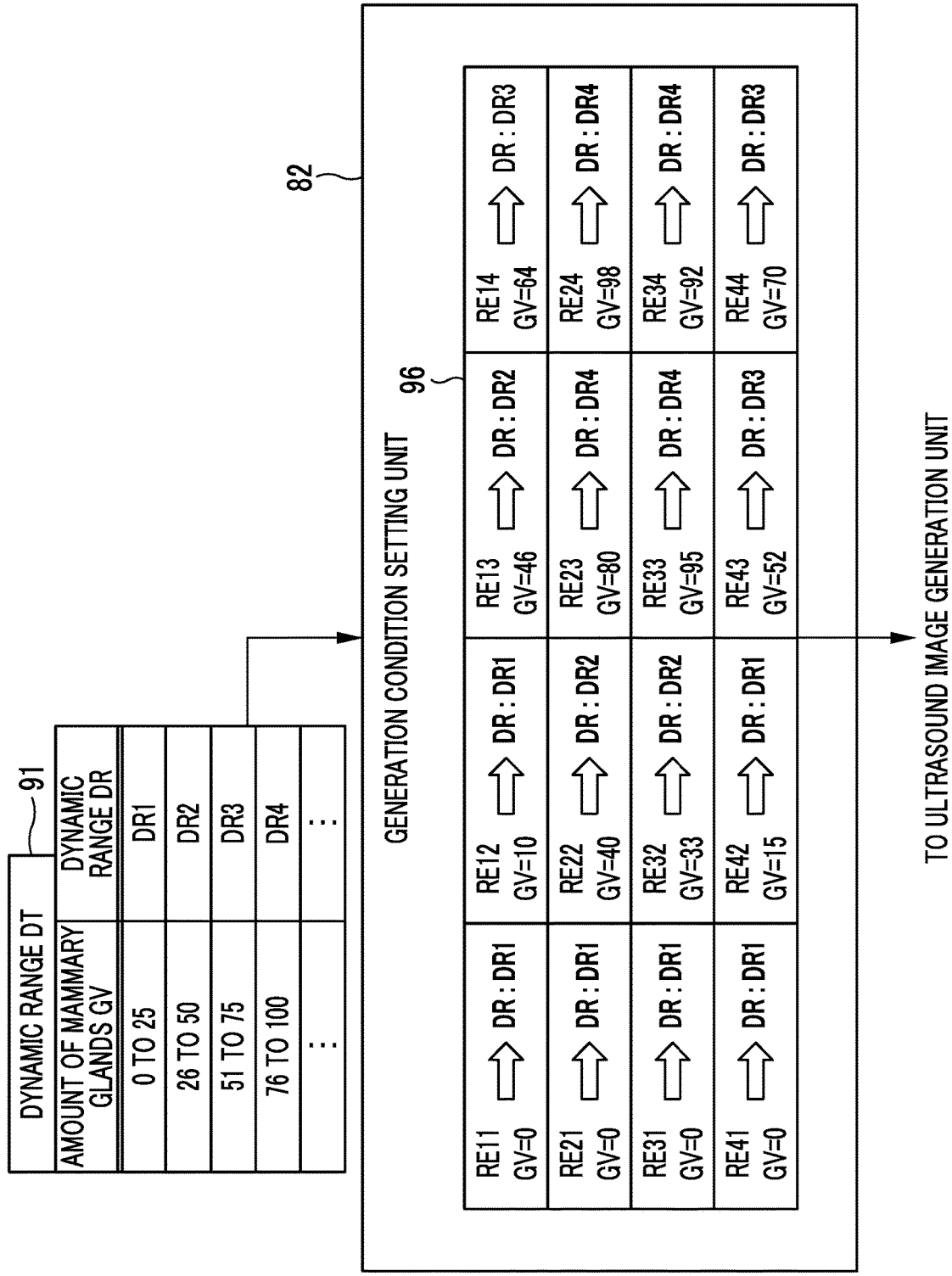
FIG. 15 is a diagram illustrating an aspect in which a dynamic range is set for each region as the generation conditions.

In FIG. 15 illustrated in Step ST12, the generation condition setting unit 82 sets the dynamic range DR for each region RE as illustrated in a table 96. For example, in the regions RE11, RE12, RE21, RE31, RE41, and RE42, since the amount of mammary glands GV is in the range of 0 to 25, the dynamic range DR is set to DR1. In the regions RE23, RE24, RE33, and RE34, since the amount of mammary glands GV is in the range of 76 to 100, the dynamic range DR is set to DR4. That is, the generation condition setting unit 82 sets the dynamic range DR for each of the plurality of regions RE such that, as the amount of mammary glands GV becomes larger, the dynamic range DR becomes wider. The generation condition setting unit 82 outputs the information of the dynamic range DR set for each region RE to the ultrasound image generation unit 83.

The ultrasound image generation unit 83 applies the amplification factor GN and the dynamic range DR from the generation condition setting unit 82 to each region RE to generate an ultrasound image. For example, the ultrasound image generation unit 83 generates an ultrasound image by multiplying the ultrasound image signal by 2 as the amplification factor GN and setting the dynamic range DR of the ultrasound image signal to the DR4 for the region RE33.

The scanning mechanism control unit 77 checks the position of the ultrasound transceiver 31, that is, the region RE scanned by the ultrasound transceiver 31. The ultrasound image generation unit 83 receives the information of the region RE scanned by the ultrasound transceiver 31 from the scanning mechanism control unit 77. Then, the ultrasound image generation unit 83 applies the amplification factor GN and the dynamic range DR corresponding to the information.

Figure 16:
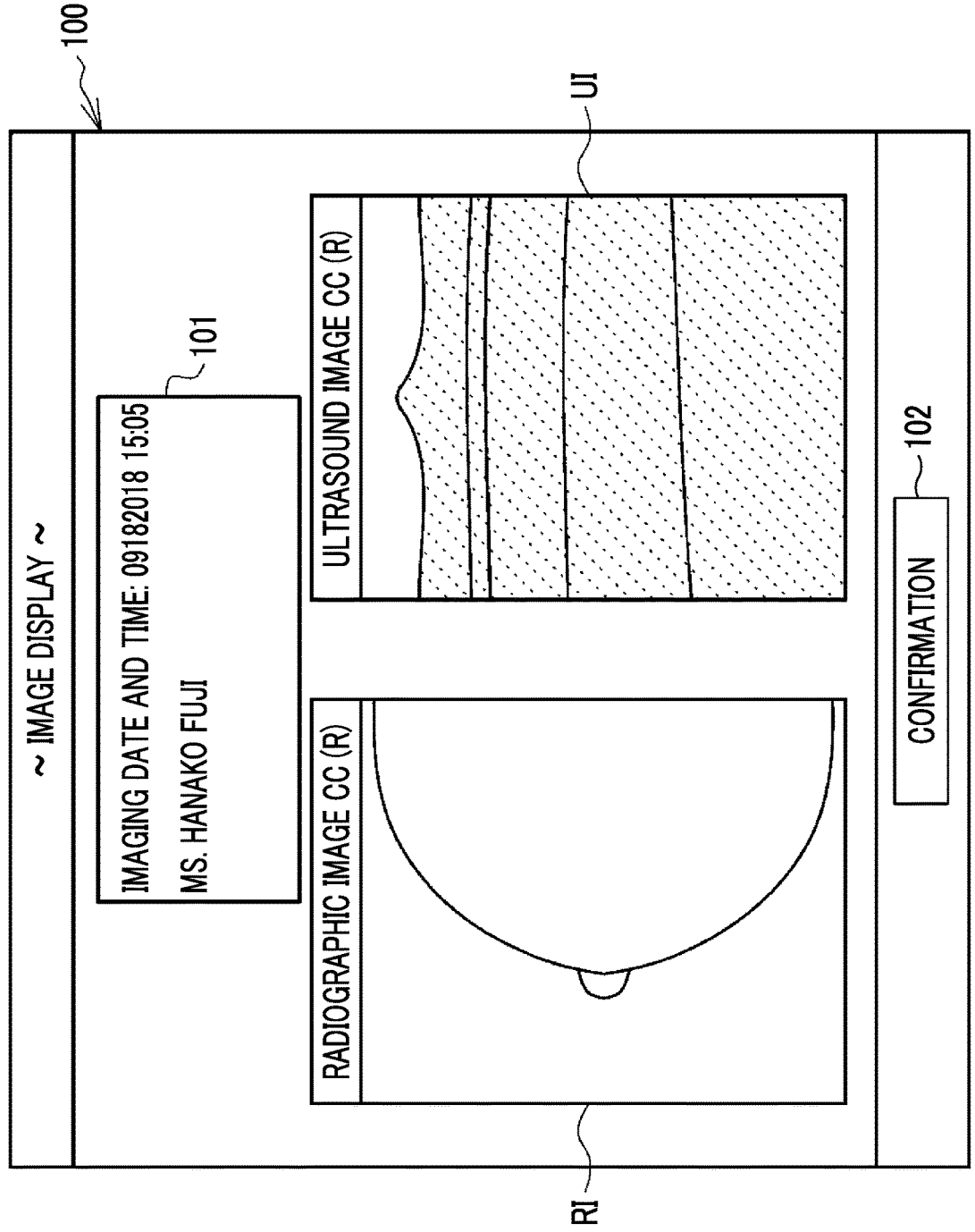
FIG. 16 is a diagram illustrating an image display screen.

The display control unit 84 displays an ultrasound image UI generated by the ultrasound image generation unit 83 and a radiographic image RI generated by the radiographic image generation unit 80 side by side on the display 64 as illustrated in an image display screen 100 in FIG. 16. It is possible to display the display tomographic planes of the ultrasound image UI on the image display screen 100 such that the display tomographic planes are switched. In addition, reference numeral 101 indicates an information display region in which information related to imaging, such as the imaging date and time or the name of the subject H, is displayed. Further, reference numeral 102 indicates a confirmation button for turning off the image display screen 100. Furthermore, "CC(R)" in each of the images RI and UI indicates that each of the images RI and UI is obtained by capturing an image of the right breast M using the CC imaging method.

The control device 12 transmits the radiographic image RI generated by the radiographic image generation unit 80 and the ultrasound image UI generated by the ultrasound image generation unit 83 to the image DB server 14 through the communication unit 63.

Figure 17:
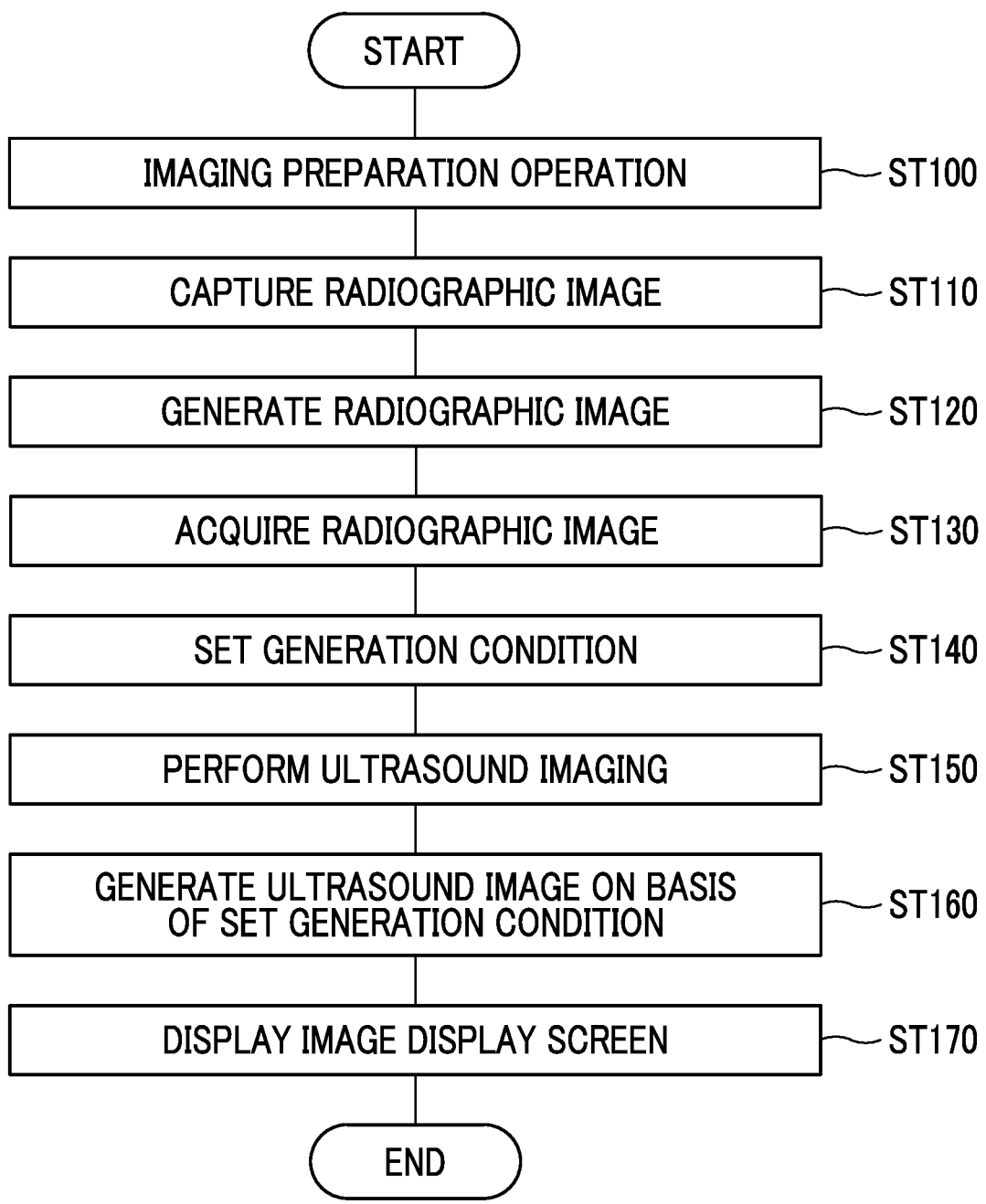
FIG. 17 is a flowchart illustrating the procedure of capturing an image of the breast using a mammography apparatus.

Next, the operation of the above-mentioned configuration will be described with reference to a flowchart illustrated in FIG. 17. The procedure of capturing the image of the breast M by the mammography apparatus 10 starts from an imaging preparation operation in Step ST100. The imaging preparation operation is performed by a radiology technician who operates the mammography apparatus 10 and is mainly related to the positioning of the breast M. For example, the imaging preparation operation is performed to guide the subject H in front of the apparatus main body 11 such that the breast M is placed on the imaging table 23. The imaging preparation operation includes an operation in which the movement mechanism 30 moves the compression plate 29 to the imaging table 23 to compress the breast M interposed between the compression plate 29 and the imaging table 23 under control of the movement mechanism control unit 78. After the imaging preparation operation ends, the radiology technician inputs a command to start imaging.

First, the radiation source control unit 75 and the detector control unit 79 operate the radiation source 25 and the radiation detector 26 to capture a radiographic image of the breast M (Step ST110). Then, the radiation detector 26 outputs a radiographic image signal to the radiographic image generation unit 80. The radiographic image generation unit 80 generates a radiographic image from the radiographic image signal (Step ST120). The radiographic image is output from the radiographic image generation unit 80 to the acquisition unit 81 and the display control unit 84.

The acquisition unit 81 acquires the radiographic image from the radiographic image generation unit 80 (Step ST130, an acquisition step). The radiographic image is output from the acquisition unit 81 to the generation condition setting unit 82.

As illustrated in FIGS. 12 to 15, the generation condition setting unit 82 sets generation conditions on the basis of the radiographic image (Step ST140, a generation condition setting step). Specifically, as illustrated in Step ST10 of FIG. 12 and FIG. 13, the generation condition setting unit 82 analyzes the radiographic image and detects the amount of mammary glands GV for each region RE of the radiographic image. Then, as illustrated in Step ST11 of FIG. 12 and FIG. 14, the amplification factor GN for each region RE is set as the generation conditions. As illustrated in Step ST12 of FIG. 12 and FIG. 15, the dynamic range DR for each region RE is set as the generation conditions. The set amplification factor GN and dynamic range DR are output from the generation condition setting unit 82 to the ultrasound image generation unit 83.

The scanning mechanism 32 moves the ultrasound transceiver 31 under the control of the scanning mechanism control unit 77 and ultrasound imaging is performed (Step ST150). Then, an ultrasound image signal is output from the ultrasound transceiver 31 to the ultrasound image generation unit 83. The ultrasound image generation unit 83 generates an ultrasound image from the ultrasound image signal on the basis of the amplification factor GN and the dynamic range DR from the generation condition setting unit 82 (Step ST160). The ultrasound image is output from the ultrasound image generation unit 83 to the display control unit 84.

As illustrated in FIG. 16, the radiographic image RI and the ultrasound image UI are displayed side by side on the display 64 by the display control unit 84 and are viewed by a radiology technician (Step ST170). In this way, one radiography and ultrasound imaging operation which is performed in a state in which the same breast M of the same subject H is compressed by the imaging table 23 and the compression plate 29 ends.

As described above, in this embodiment, the acquisition unit 81 acquires a radiographic image as radiography information in a case in which the radiographic image of the breast M is captured. Then, the generation condition setting unit 82 sets generation conditions in a case in which an ultrasound image of the breast M is generated, on the basis of the radiographic image acquired by the acquisition unit 81. The generation conditions are a major factor that determines the quality of an ultrasound image. Therefore, it is possible to set the generation conditions that contribute to improving the quality of the ultrasound image.

In addition, it is not necessary to receive the radiography result and to manually set the ultrasound image generation conditions and it is possible to change to ultrasound imaging immediately after radiography. Therefore, it is possible to reduce the imaging time of the breast M and to ease the pain of the subject H.

In this embodiment, the ultrasound image generation unit 83 generates an ultrasound image under the generation conditions set by the generation condition setting unit 82. Therefore, it is possible to generate an ultrasound image with higher quality.

The acquisition unit 81 acquires a radiographic image as the radiography conditions. The generation condition setting unit 82 analyzes the radiographic image to detect the amount of mammary glands GV and sets generation conditions corresponding to the detected amount of mammary glands GV. Since the quality of the ultrasound image depends on the amount of mammary glands GV, the quality of the ultrasound image is expected to be further improved by setting the generation conditions corresponding to the amount of mammary glands GV.

Since the generation condition setting unit 82 sets the amplification factor GN as the generation conditions, it is possible to generate an ultrasound image in which the tissues in the breast M are expressed by appropriate brightness. In addition, since the generation condition setting unit 82 sets the dynamic range DR as the generation conditions, it is possible to generate an ultrasound image in which the tissues in the breast M are expressed by appropriate grayscale values.

Here, the reflectance of the mammary glands with respect to the ultrasonic waves US is higher than that of other tissues. Therefore, in a case in which the amount of mammary glands GV is large, the ultrasonic waves US are attenuated in the mammary glands and few ultrasonic waves US reach a deep layer of the breast M (a portion of the breast M close to the imaging table 23). That is, the intensity of the ultrasound echoes UE from the deep layer is low. As a result, in a case in which the amount of mammary glands GV is large, the value of the ultrasound image signal from the deep layer is likely to be small. However, in this embodiment, the generation condition setting unit 82 sets the amplification factor GN such that it becomes higher as the amount of mammary glands GV becomes larger. Therefore, even in a case in which the amount of mammary glands GV is large, it is possible to generate an ultrasound image in which a deep layer is also expressed by appropriate brightness.

It is considered that the width of the value of the ultrasound image signal in a case in which the amount of mammary glands GV is large is greater than that in a case in which the amount of mammary glands GV is small. The generation condition setting unit 82 sets the dynamic range DR such that it becomes wider as the amount of mammary glands GV becomes larger. Therefore, it is possible to generate an ultrasound image UI which is expressed by a grayscale value corresponding to the amount of mammary glands GV.

The generation condition setting unit 82 sets the generation conditions for each of the plurality of regions RE. Therefore, it is possible to generate the ultrasound image UI under the generation conditions suitable for each region RE and to generate an ultrasound image with higher quality.

Second Embodiment

Figure 18:
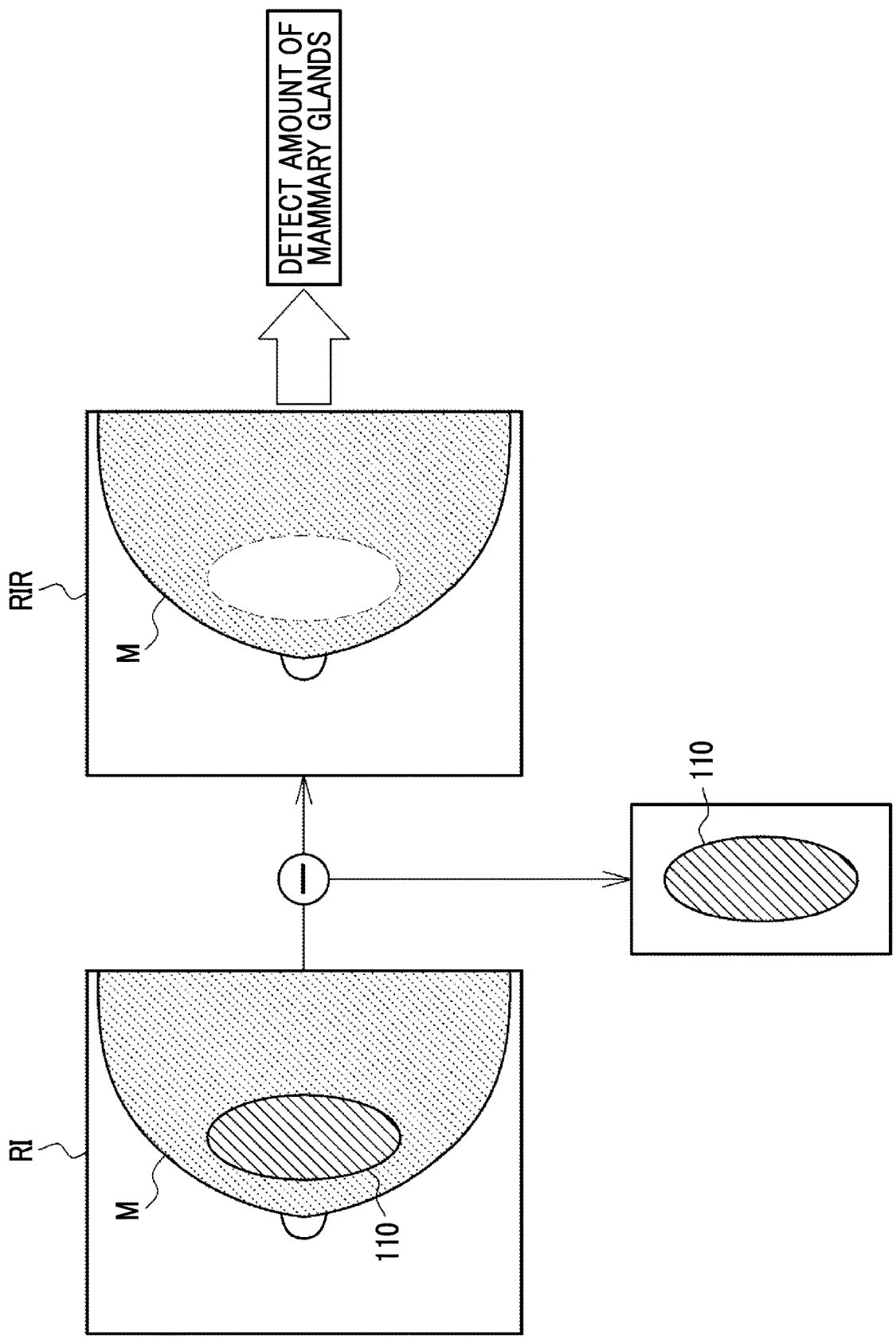
FIG. 18 is a diagram illustrating a second embodiment in which an image of an artifact is removed from a radiographic image and then the amount of mammary glands is detected.

In a second embodiment illustrated in FIG. 18, in a case in which an artifact is included in the breast M, an image of the artifact is removed from the radiographic image and then the amount of mammary glands GV is detected.

In FIG. 18, in a case in which an artifact, such as a silicon bag, is included in the breast M, an image 110 of the artifact is included in the radiographic image RI. In the radiographic image RI including the image 110 of the artifact, it is difficult to accurately detect the amount of mammary glands GV. For this reason, a generation condition setting unit according to the second embodiment extracts the image 110 of the artifact included in the radiographic image RI using a known image recognition technique and removes the extracted image 110 of the artifact from the radiographic image RI. Then, the generation condition setting unit detects the amount of mammary glands GV, using a radiographic image RIR in which the image 110 of the artifact has been removed.

As such, in the second embodiment, the generation condition setting unit removes the image 110 of the artifact from the radiographic image RI and then detects the amount of mammary glands GV. Therefore, it is possible to accurately detect the amount of mammary glands GV regardless of the presence of artifacts.

Third Embodiment

Figure 19:
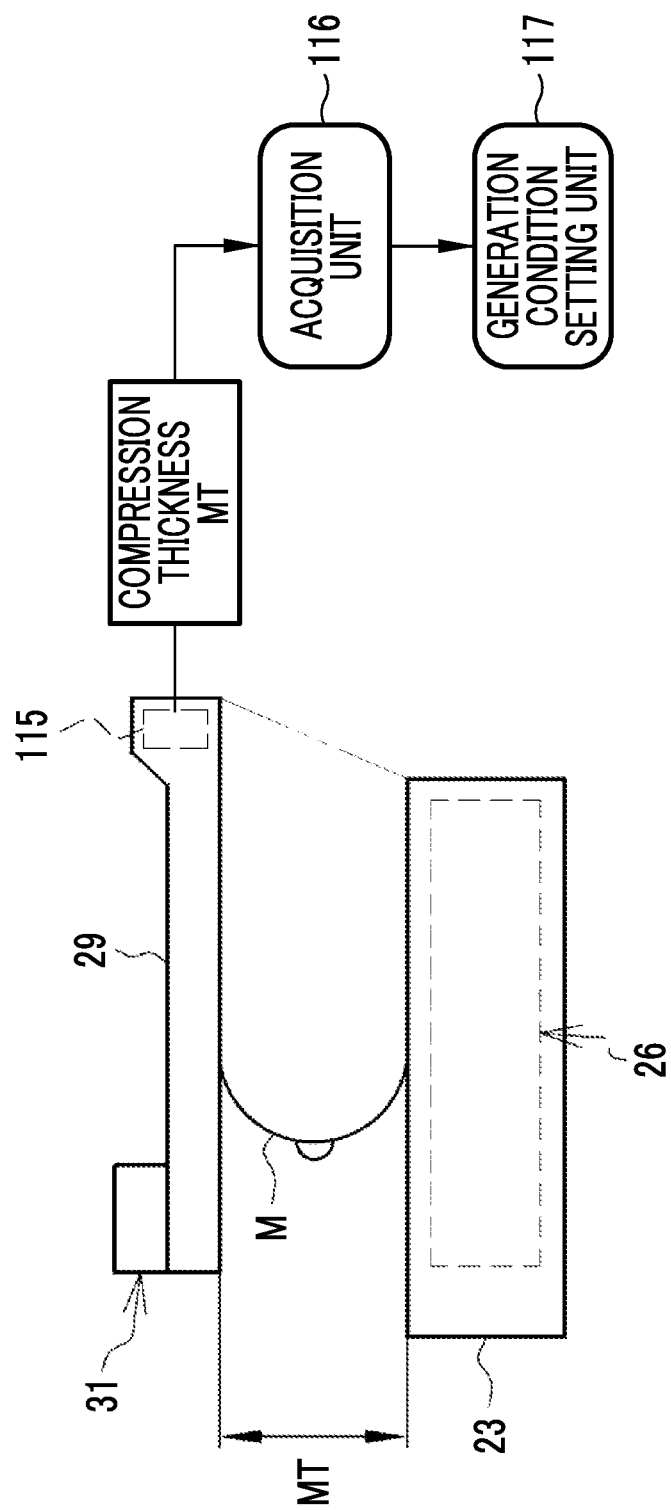
FIG. 19 is a diagram illustrating a third embodiment in which a compression thickness of the breast is acquired as radiography information.
Figures 20, 21:
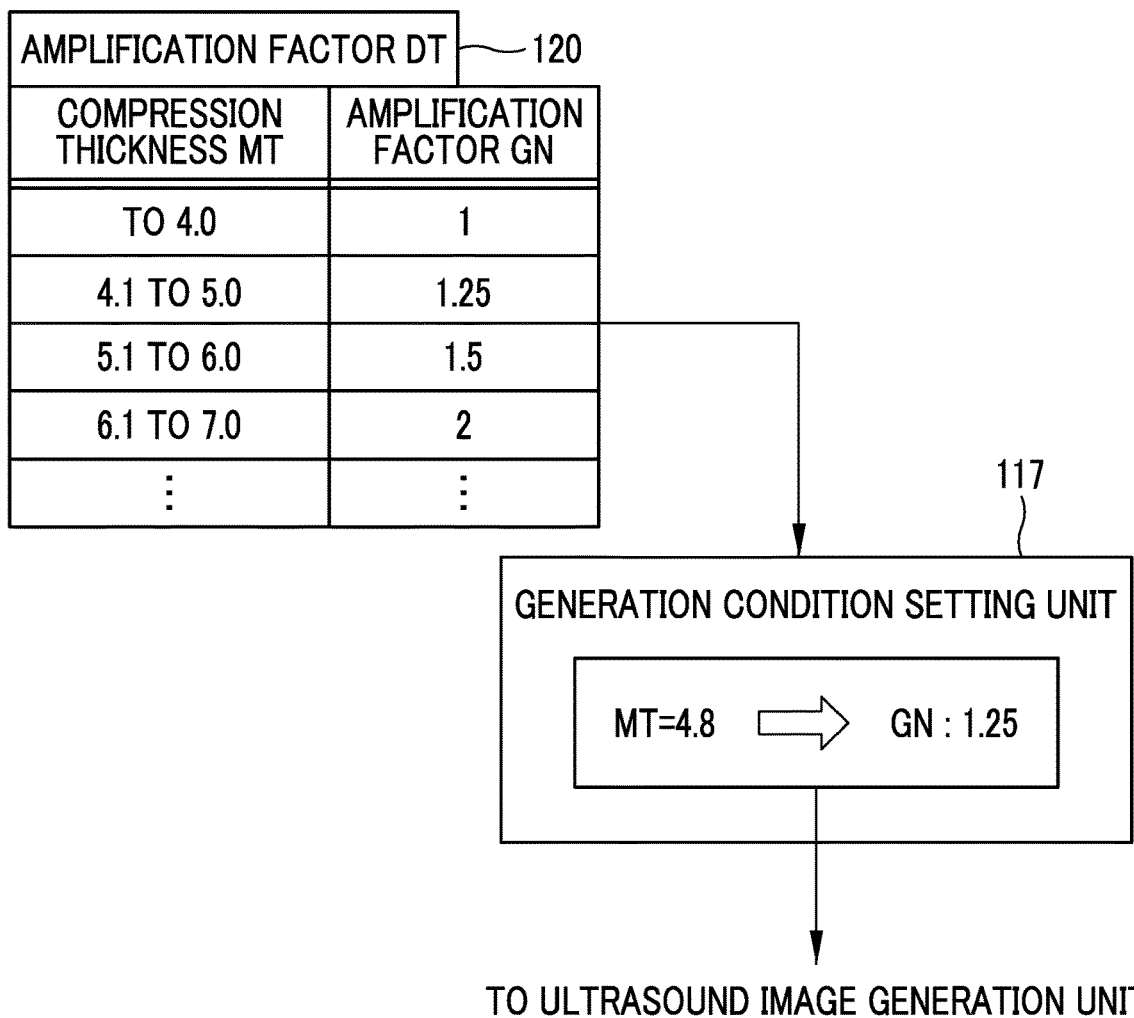
FIG. 20 is a diagram illustrating an amplification factor data table according to a third embodiment.
FIG. 21 is a diagram illustrating an aspect in which an amplification factor is set as generation conditions.

In a third embodiment illustrated in FIGS. 19 to 21, a compression thickness of the breast M during radiography is acquired as radiography information and the amplification factor GN is set on the basis of the compression thickness.

In FIG. 19, a compression plate 29 is provided with a measurement sensor 115 that measures a compression thickness MT of the breast M. The measurement sensor 115 is, for example, a linear potentiometer that measures the height of the compression plate 29 from the imaging table 23 as the compression thickness MT. For example, the measurement sensor 115 measures the compression thickness MT in 1 mm steps.

The measurement sensor 115 outputs the compression thickness MT during radiography to an acquisition unit 116. The acquisition unit 116 acquires the compression thickness MT from the measurement sensor 115 as radiography information. The acquisition unit 116 outputs the acquired compression thickness MT to a generation condition setting unit 117.

As illustrated in FIG. 20, an amplification factor GN corresponding to each range of the compression thickness MT of the breast M is registered in an amplification factor DT 120 according to the third embodiment. The amplification factor GN is 1 in a case in which the compression thickness MT is in the range of 0 to 4.0 (unit: cm). That is, no amplification is performed in this range. For example, the amplification factor GN is 1.25 in a case in which the compression thickness MT is in the range of 4.1 to 5.0, is 1.5 in a case in which the compression thickness MT is in the range of 5.1 to 6.0, and is 2 in a case in which the compression thickness MT is in the range of 6.1 to 7.0. That is, the amplification factor DT 120 is set such that, as the compression thickness MT becomes larger, the amplification factor GN becomes higher.

As illustrated in FIG. 21, the generation condition setting unit 117 sets the amplification factor GN corresponding to the compression thickness MT from the acquisition unit 116 with reference to the amplification factor DT 120. FIG. 21 illustrates an example in which the compression thickness MT is 4.8 and the amplification factor GN is set to 1.25. In the third embodiment, the amplification factor is not set for each region RE unlike the first embodiment and one amplification factor is set for the entire region. This holds for the following fourth embodiment.

As such, in the third embodiment, the acquisition unit 116 acquires the compression thickness MT of the breast M during radiography as radiography information and the generation condition setting unit 117 sets the amplification factor GN on the basis of the compression thickness MT. In addition, the generation condition setting unit 117 sets the amplification factor GN such that it becomes higher as the compression thickness MT becomes larger.

Similarly to the case in which the amount of mammary glands GV is large as in the first embodiment, in a case in which the compression thickness MT is large, the value of an ultrasound image signal in a deep layer of the breast M is likely to be small. However, in the third embodiment, the amplification factor GN is set so as to become higher as the compression thickness MT becomes larger. Therefore, even in a case in which the compression thickness MT is large, it is possible to generate an ultrasound image in which a deep layer is also expressed by appropriate brightness.

The setting of values in the amplification factor DT 120 illustrated in FIG. 20 is the same as that in, for example, FIG. 10 in the first embodiment and is just an example. In addition, the amplification factor DT 120 may not be necessarily in the form of a data table. For example, an expression in which the compression thickness MT is a parameter and the amplification factor GN is a solution may be used.

Fourth Embodiment

Figure 22:
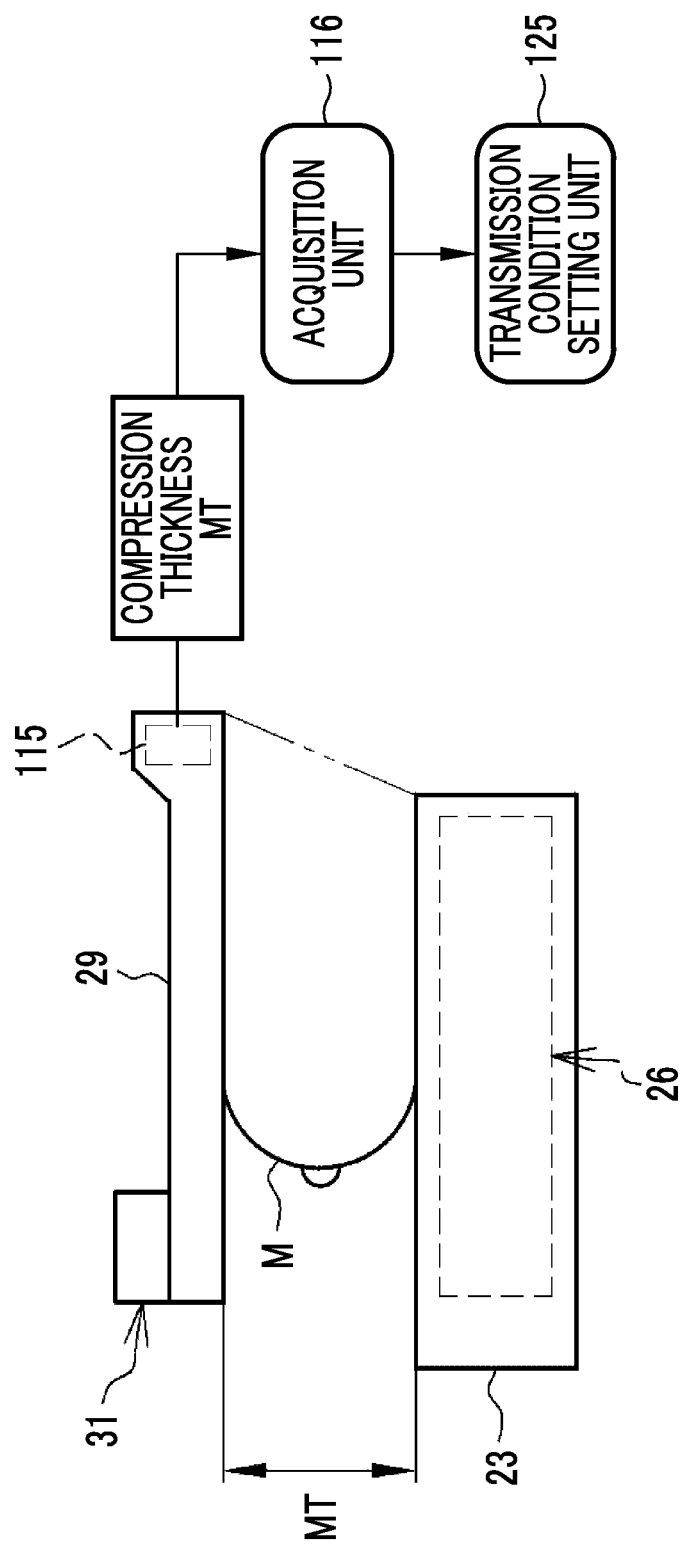
FIG. 22 is a diagram illustrating a fourth embodiment in which ultrasonic wave transmission conditions are set.
Figures 23, 24:
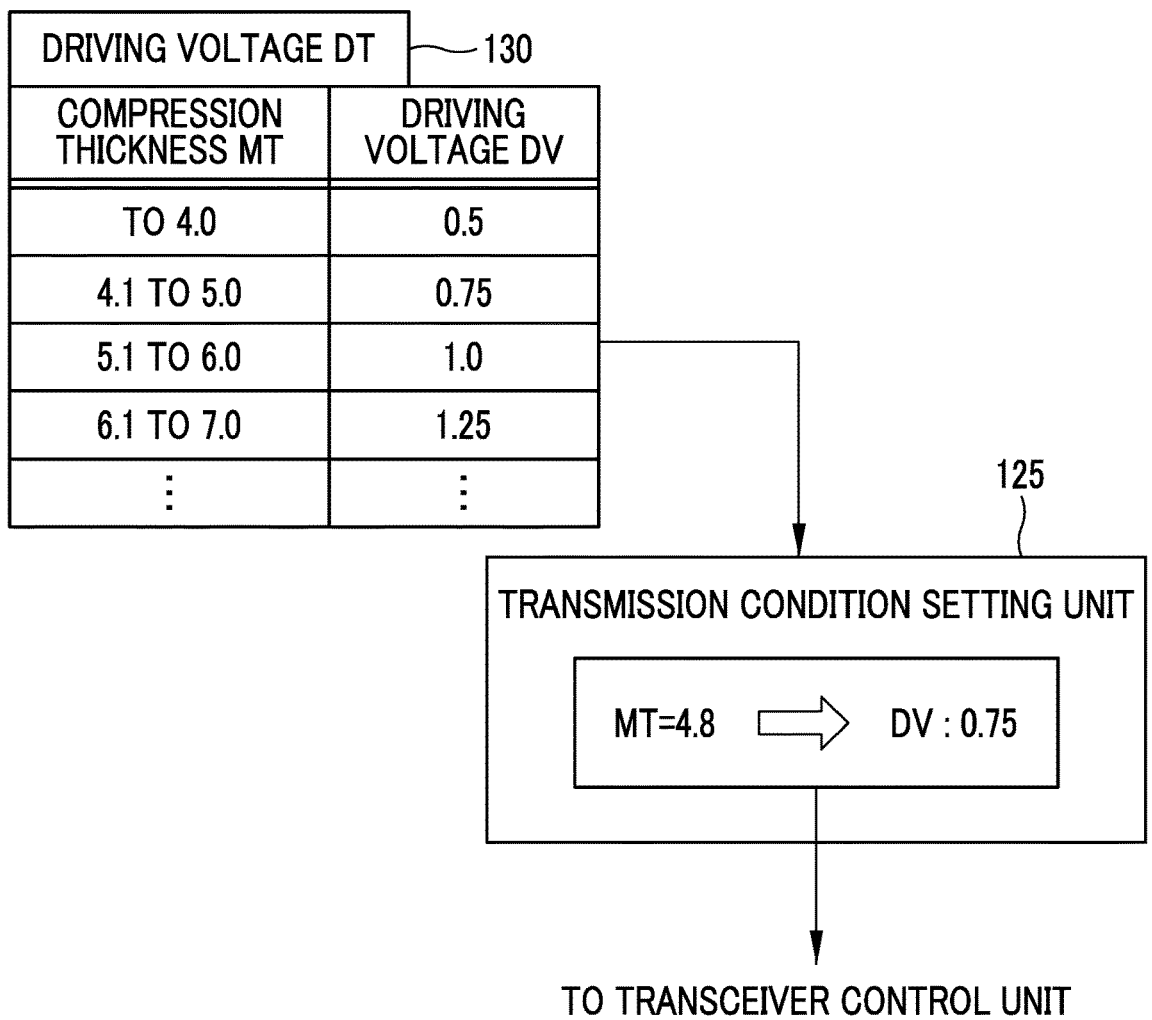
FIG. 23 is a diagram illustrating a driving voltage data table.
FIG. 24 is a diagram illustrating an aspect in which a driving voltage is set as the transmission conditions.

A fourth embodiment illustrated in FIGS. 22 to 24 is the same as the third embodiment in that the compression thickness MT of the breast M during radiography is acquired as radiography information. However, the fourth embodiment differs from the third embodiment in that the amplification factor GN is not set on the basis of the compression thickness MT and parameters for determining the depth of field of the ultrasonic waves US are set on the basis of the compression thickness MT.

Here, the depth of field of the ultrasonic waves US is a depth that the ultrasonic waves US reach and is also referred to as a depth. The parameters for determining the depth of field of the ultrasonic waves US are, for example, a driving voltage of the ultrasound transducer 51 and a driving frequency of the ultrasound transducer 51. As the driving voltage of the ultrasound transducer 51 becomes higher, the depth of field of the ultrasonic waves US becomes larger. In addition, as the driving frequency of the ultrasound transducer 51 becomes higher, the depth of field of the ultrasonic waves US becomes smaller. Next, an example in which the driving voltage of the ultrasound transducer 51 is set as the parameter for determining the depth of field of the ultrasonic waves US will be described. However, the driving frequency of the ultrasound transducer may be set in addition to or instead of the driving voltage.

In FIG. 22, in the fourth embodiment, a transmission condition setting unit 125 is provided in the CPU of the control device. The transmission condition setting unit 125 acquires the compression thickness MT of the breast M during radiography which has been measured by the measurement sensor 115 as radiography information from the acquisition unit 116. The transmission condition setting unit 125 sets a driving voltage DV (see FIG. 23) of the ultrasound transducer 51 as the transmission condition of the ultrasonic waves US on the basis of the compression thickness MT from the acquisition unit 116.

As illustrated in FIG. 23, in the fourth embodiment, a driving voltage DT 130 is stored in the storage device of the control device. The driving voltage DV of the ultrasound transducer 51 corresponding to each range of the compression thickness MT of the breast M is registered in the driving voltage DT 130. The driving voltage DV is 0.5 (the unit is, for example, kV) in a case in which the compression thickness MT is in the range of 0 to 4.0 (unit: cm). For example, the driving voltage DV is 0.75 in a case in which the compression thickness MT is in the range of 4.1 to 5.0, is 1.0 in a case in which the compression thickness MT is in the range of 5.1 to 6.0, and is 1.25 in a case in which the compression thickness MT is in the range of 6.1 to 7.0. That is, the driving voltage DT 130 is set such that, as the compression thickness MT becomes larger, the driving voltage DV becomes higher, that is, the depth of field of the ultrasonic waves US becomes larger. Further, the driving voltage DV in the driving voltage DT 130 is set to a value where the ultrasonic waves US that can sufficiently reach a deep layer of the breast M are transmitted at the corresponding compression thickness MT.

As illustrated in FIG. 24, the transmission condition setting unit 125 sets the driving voltage DV corresponding to the compression thickness MT from the acquisition unit 116 with reference to the driving voltage DT 130. The transmission condition setting unit 125 outputs the set driving voltage DV to the transceiver control unit. The transceiver control unit drives the ultrasound transducer 51 at the driving voltage DV from the transmission condition setting unit 125. FIG. 24 illustrates an example in which the compression thickness MT is 4.8 and the driving voltage DV is set to 0.75.

As such, in the fourth embodiment, the acquisition unit 116 acquires the compression thickness MT of the breast M during radiography as radiography information and the transmission condition setting unit 125 sets a parameter (the driving voltage DV of the ultrasound transducer 51) for determining the depth of field of the ultrasonic waves US as the transmission condition of the ultrasonic waves US on the basis of the compression thickness MT. Therefore, not only the generation conditions of the ultrasound image but also the transmission conditions of the ultrasonic wave US are optimized, which makes it possible to contribute to further improving the quality of an ultrasound image.

In addition, the transmission condition setting unit 125 sets the parameter such that, as the compression thickness MT becomes larger, the depth of field becomes larger. Therefore, even in a case in which the compression thickness MT is large, the ultrasonic waves US can certainly reach a deep layer of the breast M and it is possible to obtain the image information of the deep layer of the breast M.

Further, as in the first embodiment, the acquisition unit 116 may acquire the radiographic image RI as radiography information, the amount of mammary glands GV may be detected from the radiographic image RI, and the parameter for determining the depth of field may be set on the basis of the detected amount of mammary glands GV. In this case, the transmission condition setting unit 125 sets the parameter such that, as the amount of mammary glands GV becomes larger, the depth of field becomes larger.

It is possible to understand the invention described in the following Supplementary Note 1 from the fourth embodiment.

Supplementary Note 1

There is provided an information processing apparatus comprising: an acquisition unit that acquires a compression thickness of the breast in a case in which a radiographic image of the breast is captured; and a parameter setting unit that sets a parameter for determining a depth of field of ultrasonic waves transmitted to the breast in order to capture an ultrasound image, on the basis of the compression thickness acquired by the acquisition unit.

The acquisition unit 116 corresponds to the acquisition unit in Supplementary Note 1 and the transmission condition setting unit 125 corresponds to the parameter setting unit in Supplementary Note 1. In addition, the driving voltage DV corresponds to the parameter in Supplementary Note 1.

Figure 25:
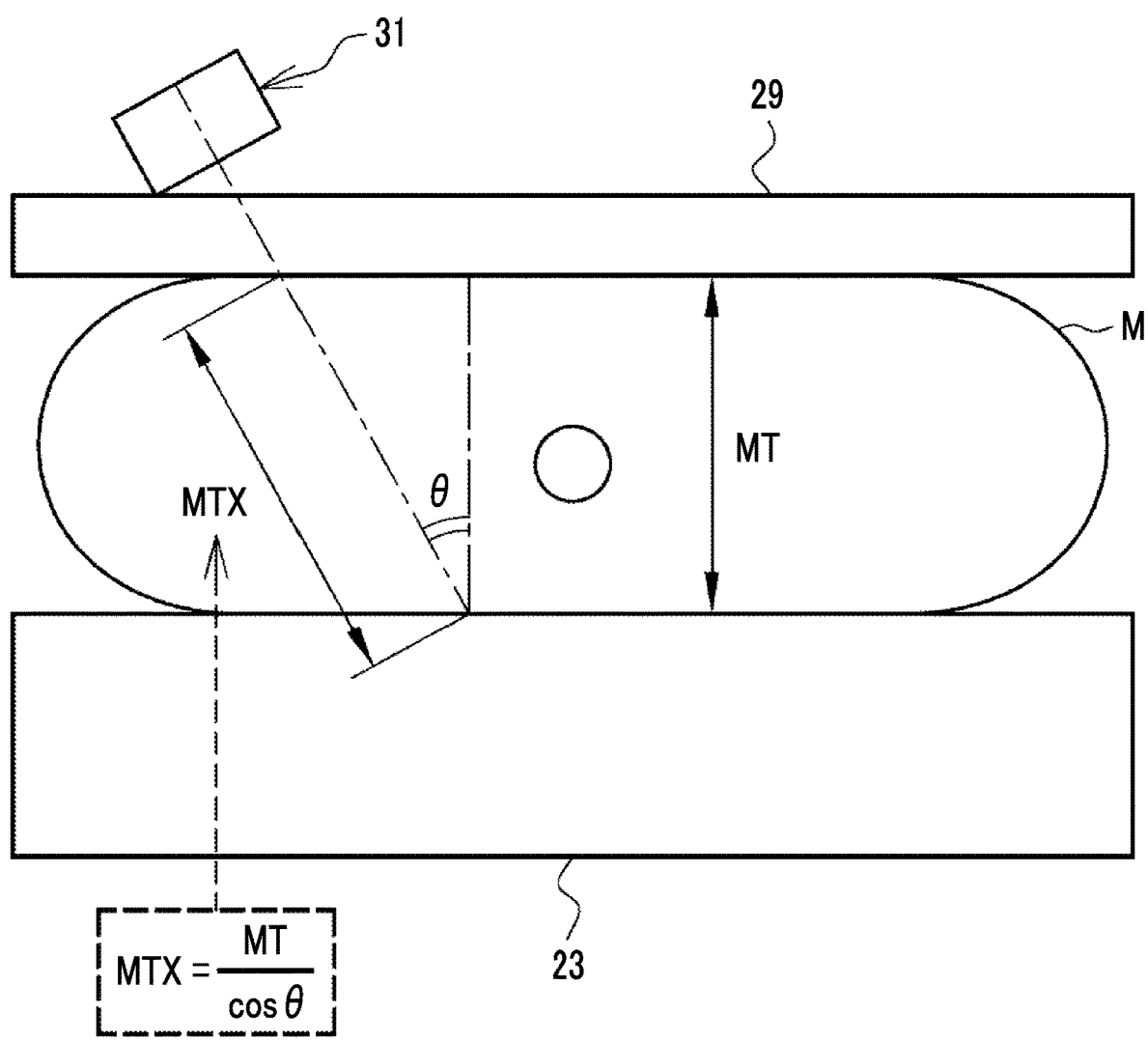
FIG. 25 is a diagram illustrating a compression thickness in a case in which ultrasound imaging is performed with an ultrasound transceiver inclined with respect to an imaging table.

In each of the above-described embodiments, it is premised that ultrasound imaging is performed in a state in which a plane forming the ultrasound imaging region 52 is parallel to a plane forming the radiography region 55. However, the technology according to the present disclosure is not limited thereto. As illustrated in FIG. 25, ultrasound imaging may be performed in a state in which the ultrasound transceiver 31 is inclined.

However, in FIG. 25, a corrected compression thickness MTX (=MT/cos θ) obtained by correcting the compression thickness MT measured by the measurement sensor 115 with an inclination angle θ of the ultrasound transceiver 31 is used. In this case, the setting of the amplification factor GN on the basis of the compression thickness MT according to the third embodiment or the setting of the parameter for determining the depth of field on the basis of the compression thickness MT according to the fourth embodiment is performed. This configuration makes it possible to set the amplification factor GN or the parameter for determining the depth of field which corresponds to the inclination of the ultrasound transceiver 31.

In addition, the inclination angle θ of the ultrasound transceiver 31 may be stored in, for example, the storage device of the control device in advance. Alternatively, a gyro sensor may be attached to the ultrasound transceiver 31 and the inclination angle θ may be calculated from the output of the gyro sensor.

In each of the above-described embodiments, the ultrasound transceiver 31 is moved by the scanning mechanism 32. However, an ultrasonographer may perform scanning with a hand-held ultrasound transceiver. In a case in which the ultrasonographer manually performs scanning with the ultrasound transceiver, for example, a pressure sensor is provided on the surface of the compression plate 29 on which the ultrasound transceiver is moved and the region RE scanned by the ultrasound transceiver is checked from the output of the pressure sensor. In addition, in a case in which the ultrasonographer manually performs scanning with the ultrasound transceiver, since the ultrasound transceiver is likely to be inclined, a gyro sensor is attached to the ultrasound transceiver and the inclination angle θ of the ultrasound transceiver is calculated from the output of the gyro sensor, as described with reference to FIG. 25.

Instead of the amount of mammary glands GV, the amount of fat may be detected. In this case, as the amount of fat becomes larger, the amplification factor GN is set to become lower and the dynamic range DR is set to become narrower. In addition, as the amount of fat becomes larger, the driving voltage DV is set to become lower.

Ultrasound imaging may be performed while compressing the breast M with different levels of compression force and elastography may be performed to detect the hardness of the tissues of the breast M on the basis of an ultrasound image obtained the ultrasound imaging.

In each of the above-described embodiments, it is premised that the technology according to the present disclosure is applied to one radiography and ultrasound imaging operation performed in a state in which the same breast M of the same subject H is compressed by the imaging table 23 and the compression plate 29. However, the technology according to the present disclosure is not limited thereto. The technology according to the present disclosure may be applied to a case in which the compressed state of the breast M is released once. For example, the technology according to the present disclosure may be applied to a case in which radiography is performed in the morning and ultrasound imaging is performed in the afternoon. However, in this case, the compression thickness MT of the breast M during radiography is stored so as to be associated with, for example, the radiographic image. Then, the compression thickness MT of the breast M during ultrasound imaging is set to be equal to the stored compression thickness MT of the breast M during radiography such that a state which is almost the same as the compressed state of the breast M during radiography is obtained.

In each of the above-described embodiments, the computer forming the control device functions as an information processing apparatus. However, the present disclosure is not limited thereto. The operation program 70 may be installed in a computer forming the image DB server 14, the terminal apparatus 15, or another apparatus such that the computer forming the image DB server 14, the terminal apparatus 15, or another apparatus functions as the information processing apparatus.

For example, the following various processors can be used as the hardware structure of processing units performing various processes, such as the radiation source control unit 75, the transceiver control unit 76, the scanning mechanism control unit 77, the movement mechanism control unit 78, the detector control unit 79, the radiographic image generation unit 80, the acquisition units 81 and 116, the generation condition setting units 82 and 117, the ultrasound image generation unit 83, the display control unit 84, and the transmission condition setting unit 125. The various processors include a central processing unit (CPU) which is a general-purpose processor executing software (operation program 70) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

It is possible to understand the invention described in the following Supplementary Note 2 from the above description.

Supplementary Note 2

There is provided an information processing apparatus comprising: an acquisition processor that acquires radiography information in a case in which a radiographic image of a breast is captured; and a generation condition setting processor that sets generation conditions in a case in which an ultrasound image of the breast is generated, on the basis of the radiography information acquired by the acquisition processor.

In the technology according to the present disclosure, the above-mentioned various embodiments and various modification examples may be combined with each other. In addition, the present disclosure is not limited to the above-described embodiments and various configurations can be used without departing from the scope and spirit of the present disclosure. Further, the technology according to the present disclosure may be applied to a storage medium that temporarily stores the program in addition to the program.

What is claimed is:

1. An information processing apparatus comprising:
a memory; and
a processor coupled to the memory and configured to:
control a breast imaging apparatus including a radiation source, a radiation detector, a ultrasound transceiver and a compression mechanism, to capture a radiographic image of a breast by compressing the breast by the compression mechanism and detecting radiation emitted from the radiation source and that has transmitted through the breast by the radiation detector;
divide the radiographic image into a plurality of regions and a quantity of the plurality of regions is predetermined;
acquire an amount of mammary glands in each of the plurality of regions of the radiographic image by analyzing each of the plurality of regions of the radiographic image;
set generation conditions for each of ultrasonic imaging regions corresponding to each of the plurality of regions of the radiographic image, wherein the generation conditions for each of the ultrasonic imaging regions are based on the amount of mammary glands in a corresponding region of the radiographic image; and
control the breast imaging apparatus to generate an ultrasound image of the breast on the basis of the generation conditions, while maintaining compression of the breast by the compression mechanism from acquisition of the radiographic image.

2. The information processing apparatus according to claim 1, wherein the processor is configured to: in a case in which an artifact is included in the breast, remove the artifact from the radiographic image and detect the amount of mammary glands in each of the plurality of regions of the radiographic image.

3. The information processing apparatus according to claim 1, wherein the processor is configured to:
acquire, as the radiography information, a compression thickness of the breast for each of the plurality of regions of the radiographic image.

4. The information processing apparatus according to claim 1, wherein the processor is configured to:
set, as the generation conditions, at least one of an amplification factor of an ultrasound image signal which is an electric signal corresponding to ultrasound echoes reflected from the breast in a case in which ultrasonic waves are transmitted to the breast or a dynamic range which is a width of a grayscale value of the ultrasound image assigned to a value of the ultrasound image signal.

5. The information processing apparatus according to claim 4, wherein the processor is configured to:
set the amplification factor such that, as the amount of mammary glands becomes larger, the amplification factor becomes higher.

6. The information processing apparatus according to claim 4, wherein the processor is configured to:
set the dynamic range such that, as the amount of mammary glands becomes larger, the dynamic range becomes wider.

7. The information processing apparatus according to claim 1, wherein the processor is configured to:
acquire as the radiography information, a compression thickness of the breast for each of the plurality of regions of the radiographic image is captured,
set as the generation conditions, at least one of an amplification factor of an ultrasound image signal which is an electric signal corresponding to ultrasound echoes reflected from the breast in a case in which ultrasonic waves are transmitted to the breast or a dynamic range which is a width of a grayscale value of the ultrasound image assigned to a value of the ultrasound image signal, and
set the amplification factor such that, as the compression thickness becomes larger, the amplification factor becomes higher.

8. The information processing apparatus according to claim 1, wherein the processor is configured to:
set transmission conditions of the ultrasonic waves transmitted to the breast on the basis of the radiography information.

9. The information processing apparatus according to claim 8, wherein the processor is configured to acquire as the radiography information, a compression thickness of the breast for each of the plurality of regions of the radiographic image, and set a parameter for determining a depth of field of the ultrasonic waves as the transmission conditions.

10. The information processing apparatus according to claim 9, wherein the processor is configured to:

set the parameter such that, as the compression thickness becomes larger, the depth of field becomes larger.

11. A non-transitory computer-readable storage medium storing a program that causes a computer to perform information processing, the information processing comprising:

controlling a breast imaging apparatus including a radiation source, a radiation detector, a ultrasound transceiver and a compression mechanism, to capture a radiographic image of a breast by compressing the breast by the compression mechanism and detecting radiation emitted from the radiation source and that has transmitted through the breast by the radiation detector;

dividing the radiographic image into a plurality of regions and a quantity of the plurality of regions is predetermined;

acquiring an amount of mammary glands in each of the plurality of regions of the radiographic image by analyzing each of the plurality of regions of the radiographic image;

setting generation conditions for each of ultrasonic imaging regions corresponding to each of the plurality of regions of the radiographic image, wherein the generation conditions for each of the ultrasonic imaging regions are based on the amount of mammary glands in a corresponding region of the radiographic image; and controlling the breast imaging apparatus to generate an ultrasound image of the breast on the basis of the generation conditions, while maintaining compression of the breast by the compression mechanism from acquisition of the radiographic image.

12. A breast imaging method comprising:

capturing a radiographic image of a breast by compressing the breast and by detecting radiation that has transmitted through the breast;

dividing the radiographic image into a plurality of regions and a quantity of the plurality of regions is predetermined;

acquiring an amount of mammary glands in each of the plurality of regions of the radiographic image by analyzing each of the plurality of regions of the radiographic image;

setting generation conditions for each of ultrasonic imaging regions corresponding to each of the plurality of regions of the radiographic image, wherein the generation conditions for each of the ultrasonic imaging regions are based on the amount of mammary glands in a corresponding region of the radiographic image; and controlling the breast imaging apparatus to generate an ultrasound image of the breast on the basis of the generation conditions, while maintaining compression of the breast by the compression mechanism from acquisition of the radiographic image.

13. A breast imaging apparatus comprising:

a radiation source that emits radiation;

a radiation detector that detects radiation transmitted through a breast;

a compression mechanism configured to compress the breast;

an ultrasound transceiver including ultrasound transducers that transmit ultrasonic waves to the breast and receive ultrasound echoes from the breast;

a memory; and a processor coupled to the memory and configured to:

capture a radiographic image of the breast by compressing the breast by the compression mechanism and detecting radiation emitted from the radiation source and that has transmitted through the breast by the radiation detector;

divide the radiographic image into a plurality of regions and a quantity of the plurality of regions is predetermined;

acquire an amount of mammary glands in each of the plurality of regions of the radiographic image;

set generation conditions for each of ultrasonic imaging regions corresponding to each of the plurality of regions of the radiographic image, wherein the generation conditions for each of the ultrasonic imaging regions are based on the amount of mammary glands in a corresponding region of the radiographic image; and generate an ultrasound image of the breast on the basis of the generation conditions, while maintaining compression of the breast by the compression mechanism from acquisition of the radiographic image.

* * * * *